(12) United States Patent
Nesvadba et al.

(10) Patent No.: US 8,969,577 B2
(45) Date of Patent: Mar. 3, 2015

(54) CURABLE COMPOSITION COMPRISING A THERMOLATENT BASE

(75) Inventors: Peter Nesvadba, Marly (CH); Lucienne Bugnon Folger, Pfeffingen (CH); Ralf Knischka, Neustadt (DE)

(73) Assignee: BASF SE, Ludwigshafen (DE)

( * ) Notice: Subject to any disclaimer, the term of this patent is extended or adjusted under 35 U.S.C. 154(b) by 465 days.

(21) Appl. No.: 13/130,331

(22) PCT Filed: Nov. 18, 2009

(86) PCT No.: PCT/EP2009/065394
§ 371 (c)(1),
(2), (4) Date: Jun. 21, 2011

(87) PCT Pub. No.: WO2010/057922
PCT Pub. Date: May 27, 2010

(65) Prior Publication Data
US 2011/0245375 A1    Oct. 6, 2011

(30) Foreign Application Priority Data

Nov. 24, 2008 (EP) .................................... 08169738

(51) Int. Cl.
| | | |
|---|---|---|
| C07D 213/74 | (2006.01) |
| C07D 215/38 | (2006.01) |
| C08G 59/50 | (2006.01) |
| C08G 59/68 | (2006.01) |
| C08L 63/00 | (2006.01) |
| C08G 59/42 | (2006.01) |

(52) U.S. Cl.
CPC ............ C07D 213/74 (2013.01); C07D 215/38 (2013.01); C08G 59/4246 (2013.01); C08G 59/686 (2013.01); C08L 63/00 (2013.01)
USPC ........... 546/312; 525/408; 546/159; 546/171; 546/297; 523/400

(58) Field of Classification Search
CPC .. C07D 213/74; C07D 215/38; C08G 59/686; C08G 59/4246; C08L 63/00
USPC .......... 523/400; 525/408; 546/159, 312, 171, 546/297
See application file for complete search history.

(56) References Cited

U.S. PATENT DOCUMENTS

| | | | |
|---|---|---|---|
| 3,165,527 A | 1/1965 | Poe | |
| 3,192,216 A | 6/1965 | Poe | |
| 3,553,292 A * | 1/1971 | Stahly et al. .................... 525/26 |
| 3,709,904 A * | 1/1973 | Tomalia et al. ................ 548/233 |
| 3,784,508 A * | 1/1974 | Tomalia et al. ................ 528/117 |
| 3,819,626 A | 6/1974 | Kobzina | |
| 3,938,985 A | 2/1976 | Kobzina | |
| 4,088,496 A | 5/1978 | Merkel | |
| 4,147,712 A * | 4/1979 | Williams et al. ............... 556/423 |
| 4,156,677 A * | 5/1979 | Williams et al. ............... 523/213 |
| 4,189,543 A | 2/1980 | Doorakian | |
| 4,218,513 A * | 8/1980 | Williams et al. ............... 428/419 |
| 4,316,621 A * | 2/1982 | Petitpierre ..................... 503/216 |
| 4,902,760 A * | 2/1990 | Arita et al. ..................... 525/504 |
| 6,174,985 B1 * | 1/2001 | Hall-Goulle ................... 528/117 |
| 6,699,651 B1 | 3/2004 | Goswami et al. | |
| 2003/0171304 A1 | 9/2003 | Holzeman | |
| 2005/0209260 A1 | 9/2005 | Broka | |
| 2008/0058383 A1 | 3/2008 | Jernstedt | |

FOREIGN PATENT DOCUMENTS

| | | |
|---|---|---|
| DE | 3530252 A1 | 3/1986 |
| EP | 0 118 078 A2 | 9/1984 |
| EP | 0 120 661 A2 | 10/1984 |
| EP | 0535521 A | 4/1993 |
| EP | 1103553 A | 5/2001 |
| GB | 901311 A | 7/1962 |
| GB | 998949 | 7/1965 |
| JP | 50 155625 A | 12/1975 |
| JP | 62161819 A | 7/1987 |
| JP | 04 275278 A | 9/1992 |
| JP | 05078502 A * | 3/1993 |
| JP | 07 138237 A | 5/1995 |
| JP | 2003021883 A * | 1/2003 |
| JP | 2003529643 A | 10/2003 |
| JP | 2004 346016 A | 12/2004 |
| JP | 2007509116 A | 4/2007 |
| WO | 98/04531 A | 2/1998 |
| WO | 98/04531 A1 | 2/1998 |
| WO | 01/74798 A1 | 10/2001 |
| WO | 2004503562 A | 2/2004 |
| WO | 2007/030582 A | 3/2007 |

OTHER PUBLICATIONS

English Language Abstract of JP 2004 346016 Dec. 9, 2004.
English Language Abstract of JP 04 275278 Sep. 30, 1992.
English Language Abstract of JP 07 138237 May 30, 1995.
Werbel, et al. J. Med. Chem. vol. 14, No. 1, (1971) pp. 10-16.
Doan et al., J. Pharm. Sci. vol. 54, No. 11,(1965) pp. 1605-1609.
English Language Abstract of DE 35 30 252 Mar. 6, 1986.
English Lang. Abst of JP 62161819, (1987).

* cited by examiner

*Primary Examiner* — Randy Gulakowski
*Assistant Examiner* — Ha Nguyen
(74) *Attorney, Agent, or Firm* — Shruti Costales

(57) ABSTRACT

The present invention relates to curable compositions comprising a thermolatent amidine base and an organic material which is polymerizable or crosslinkable with a basic or nucleophilic catalyst. In particular, the invention relates to curable coating compositions, especially powder coating compositions, and curable adhesive compositions, as well as to the use a thermolatent amidine base as a curing catalyst for thermally induced base-catalyzed polymerization or crosslinking reactions.

11 Claims, No Drawings

CURABLE COMPOSITION COMPRISING A THERMOLATENT BASE

The present invention relates to curable compositions comprising a thermolatent amidine base and an organic material which is polymerisable or crosslinkable with a basic or nucleophilic catalyst. In particular, the invention relates to curable coating compositions, especially powder coating compositions, and curable adhesive compositions, as well as to the use a thermolatent amidine base as a curing catalyst for thermally induced base-catalysed polymerisation or crosslinking reactions.

Compounds from which bases are released by heating are referred to as thermolatent bases. Thermolatent bases are employed in various systems designed so that the bases released by heating can function therein. Examples of such systems include heat-developable photographic materials, heat sensitive recording materials, anion-polymerisable adhesives, film formation by coating, sealing materials, caulking materials, and the like.

Typical thermolatent bases for use in various types of image-forming materials for which heat is utilized are salts of carboxylic acids and organic bases, as described, for example, in GB 998,949 (trichloroacetic acid salts), U.S. Pat. No. 6,699,651 (α-sulfonylacetic acid salts). DE-A-35 30 252 describes salts comprising as a thermolatent base a protonated guanidine, an amidine or a cyclic derivative thereof. The use of these salts stems from the fact that decarboxylation of the carboxylic acids by heating results in the release of the organic bases. Other thermolatent bases include 2-carboxycarboxamide derivatives disclosed in U.S. Pat. No. 4,088,496, hydroxamic acid carbamates disclosed in EP-A-0 120 661 and aldoxime carbamates disclosed in EP-A-0 118 078.

WO 98/04531 discloses curable mixtures based on epoxy resins comprising a N-alkoxy-carbonyl imidazole as a curing catalyst which release an imidazole derivative by decarboxylation. U.S. Pat. No. 4,189,543 also describes the use of such compounds in making polyurethane foams.

Curable compositions comprising a thermolatent base as a curing catalyst could be preformulated. In order to inhibit undesired premature curing during storage of preformulated compositions comprising a curing catalyst there is a continuing need for thermolatent bases exhibiting good stability during storage in curable compositions but in addition rapid conversion into the active bases when heated at the temperature of use.

It has now been found that certain low basicity substituted amidines release a cyclic and significantly more basic or nucleophilic amidine when exposed to an elevated temperature.

These cyclic amidines are sufficiently basic or nucleophilic to initiate a large number of base-catalysed polymerisation and crosslinking reactions.

Accordingly, the present invention is directed to a curable composition comprising (A) an organic material which is polymerisable or crosslinkable with a basic or nucleophilic catalyst and (B) a compound of the formula

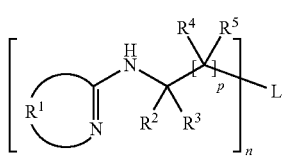

(I)

wherein $R^1$ forms together with the carbon and nitrogen atom, it is linked to, a mono- or polycyclic $C_2$-$C_{20}$ ring system, which may further contain one or more heteroatoms of O, S and/or N and/or may be unsubstituted or substituted by $C_1$-$C_{18}$alkyl; $C_1$-$C_{18}$alkyl, which is substituted by E and/or interrupted by D; $C_5$-$C_{12}$cycloalkyl; which is substituted by E and/or interrupted by D; $C_5$-$C_{12}$cycloalkenyl; $C_2$-$C_{18}$alkenyl; $C_2$-$C_{18}$alkynyl; $C_6$-$C_{18}$aryl; $C_6$-$C_{18}$aryl, which is substituted by G; $C_2$-$C_{18}$heteroaryl; $C_2$-$C_{18}$heteroaryl, which is substituted by G; $C_1$-$C_{18}$alkoxy; $C_1$-$C_{18}$alkoxy, which is substituted by E and/or interrupted by D; $C_1$-$C_{18}$alkylthio; $C_1$-$C_{18}$alkylthio, which is substituted by E and/or interrupted by D; $C_7$-$C_{18}$aralkyl; $C_7$-$C_{18}$aralkyl, which is substituted by G; halogen; oxo; OH; SH; CN; $NH_2$; $NO_2$; COOH; $NHR^6$; $NR^7R^8$; $CONH_2$; $CONR^9R^{10}$; $COR^{11}$; $C(O)OR^{12}$; $SO_2R^{13}$; $SO_3R^{14}$; $SO_2NHR^{15}$; $SO_2NR^{16}R^{17}$;

or said ring system is substituted by one or more groups of formula

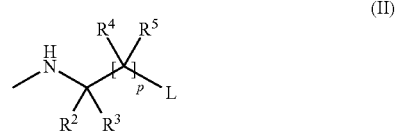

(II)

$R^2$, $R^3$, $R^4$ and $R^5$ are independently of each other and in each occurrence H; $C_1$-$C_{18}$alkyl; $C_1$-$C_{18}$alkyl, which is substituted by E and/or interrupted by D; $C_5$-$C_{12}$cycloalkyl; $C_5$-$C_{12}$cycloalkyl, which is substituted by E; $C_6$-$C_{12}$aryl; $C_6$-$C_{18}$aryl, which is substituted by G; $C_2$-$C_{18}$heteroaryl; $C_2$-$C_{18}$heteroaryl, which is substituted by G; $C_1$-$C_{18}$alkoxy; $C_1$-$C_{18}$alkoxy, which is substituted by E and/or interrupted by D; $C_7$-$C_{18}$aralkyl; $C_7$-$C_{18}$aralkyl, which is substituted by G; $NHR^{18}$, $NR^{19}R^{20}$, COOH;

or $R^2$ and $R^3$, $R^4$ and $R^5$, or $R^2$ and $R^4$ form an organic bridging group completing, together with the carbon atom, they are linked to, a carbocyclic or heterocyclic ring of 5 to 12 ring atoms in total;

or two of $R^5$, which are linked to adjacent carbon atoms, form an organic bridging group completing, together with the carbon atom, they are linked to, a carbocyclic or heterocyclic ring of 5 to 12 ring atoms in total;

D is —CO—; —COO—; —S—; —SO—; —$SO_2$—; —O—; —$NR^{21}$—; —$SiR^{22}R^{23}$—; —$POR^{24}$—; —$CR^{25}$=$CR^{26}$—; or —C≡C—; E is $OR^{27}$; $SR^{28}$; $SOR^{29}$; $SO_2R^{30}$; $NR^{31}R^{32}$; $COR^{33}$; $COOR^{34}$; $CONR^{35}R^{36}$; $PO(R^{37})_2$; $Si(R^{38})_3$; CN; or halogen; and G is E or $C_1$-$C_{18}$alkyl;

$R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$ and $R^{38}$ are independently of each other $C_1$-$C_{18}$alkyl; $C_1$-$C_{18}$alkyl, which is interrupted by —O—; $C_6$-$C_{18}$aryl; $C_6$-$C_{18}$aryl, which is substituted by $C_1$-$C_{18}$alkyl or $C_1$-$C_{18}$alkoxy; $C_7$-$C_{18}$aralkyl; $C_7$-$C_{18}$aralkyl, which is substituted by G; $C_2$-$C_{18}$heteroaryl;

or $R^7$ and $R^8$, $R^9$ and $R^{10}$, $R^{16}$ and $R^{17}$, $R^{19}$ and $R^{20}$, $R^{31}$ and $R^{32}$, or $R^{35}$ form an organic bridging group completing, together with the nitrogen atom, they are linked to, a heterocyclic ring of 5 to 7 ring atoms in total;

L is a n-valent leaving group, n is an integer of 1, 2, 3 or 4; and p is an integer of 1, 2, 3 or 4.

The compounds of formula (I) are essentially inactive at room temperature or at slightly elevated temperature and do not promote polymerisation until the composition according to the invention is heated. At elevated temperatures they release a compound of the formula (V) according to the following reaction scheme:

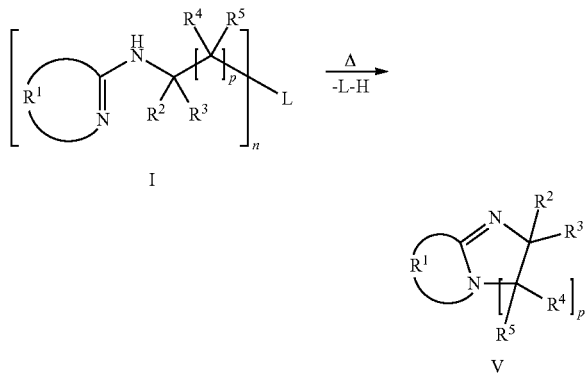

The compounds of formula (V) contain the structure of a cyclic amidine and are therefore sufficiently basic or nucleophilic to initiate a large number of base-catalysed polymerisation or crosslinking reactions. The temperature range where these bases are released and where they are active may be varied within a wide range by the choice of the substitution pattern.

Therefore, compounds of formula (I) enable to prepare so-called one-pot systems with base-polymerisable oligomers or monomers having an extremely long storage life without special precautions. In addition, such systems offer an advantage in terms of reduced handling prior immediate use and lower amounts of waste due to better pot-life. The systems may be formulated with little or no solvent, since the compounds can be dissolved in the monomers or oligomers without being affected. These systems may be employed for numerous purposes, especially for coatings, more especially for powder coatings.

At elevated temperatures, the thermolatent bases catalyse the reaction in form of their released bases. Typically, reaction temperatures required to activate the catalyst may be of from about 50° C. to about 250° C. The preferred temperature range is of from about 80° C. to about 150° C., more preferable of from about 110° C. to about 130° C.

The term "thermolatent base", also designated as "thermal base precursor", refers to a neutral or weakly basic or weakly nucleophilic compound which releases a basic or nucleophilic compound upon heating.

In a preferred embodiment the invention is directed to a curable composition comprising as a component (B) a compound of formula (I), wherein, if n is 1, L is halogen, OH, $OR^{40}$, $SR^{40}$, $OCOR^{40}$, $OCOOR^{41}$, $OCONR^{42}R^{43}$, $OCANR^{42}R^{43}$, $OSO_2R^{40}$, $OSO_3R^{40}$, $NR^{42}R^{43}$, $S^+R^{42}R^{43}X^-$, $N^+R^{42}R^{43}X^-$, $P^+R^{42}R^{43}R^{44}X^-$; $NHCOR^{40}$, $N(COR^{45})_2$, $NHSO_2R^{40}$, $NHSO_3R^{40}$, $SO_2R^{40}$, $OP(NR^{42}R^{43})_2$, $OPO(NR^{42}R^{43})_2$, $OP(OR^{40})_2$, $OPO(OR^{40})_2$, $OPO(OR^{46})(OR^{47})$, $OSi(R^{40})_3$; wherein $R^{40}$, $R^{42}$, $R^{43}$, $R^{44}$, $R^{45}$, $R^{46}$ and $R^{47}$ are independently of each other H, $C_1$-$C_{18}$alkyl or $C_1$-$C_{18}$alkyl, which is substituted by E and/or interrupted by D; $C_5$-$C_{12}$cycloalkyl, $C_5$-$C_{12}$cycloalkyl, which is substituted by E and/or interrupted by D; $C_6$-$C_{18}$aryl; $C_6$-$C_{18}$aryl, which is substituted by G; $C_7$-$C_{18}$aralkyl; $C_7$-$C_{18}$aralkyl, which is substituted by G; $C_2$-$C_{18}$heteroaryl; $C_2$-$C_{18}$heteroaryl, which is substituted by G; or $R^{42}$ and $R^{43}$ form an organic bridging group completing, together with the nitrogen atom, they are linked to, a heterocyclic ring of 5 to 7 ring atoms in total; or two of $R^{45}$ form a bridging group completing, together with the —OC—N—CO— group, they are linked to, a heterocyclic ring of 5 to 7 ring atoms in total;

$R^{41}$ is $C_1$-$C_{18}$alkyl or $C_1$-$C_{18}$alkyl, which is substituted by E and/or interrupted by D;

$C_5$-$C_{12}$cycloalkyl, $C_5$-$C_{12}$cycloalkyl, which is substituted by E and/or interrupted by D;

$C_6$-$C_{18}$aryl; $C_6$-$C_{18}$aryl, which is substituted by G; $C_2$-$C_{18}$heteroaryl; $C_2$-$C_{18}$heteroaryl, which is substituted by G;

$X^-$ is halide, hydroxide, $C_1$-$C_{18}$alkylsulfonate, $C_6$-$C_{18}$arylsulfonate, $R^{48}COO^-$, $HSO_4^-$ ½ $SO_4^{2-}$, wherein $R^{48}$ is H, $C_1$-$C_{18}$alkyl or $C_1$-$C_{18}$alkyl, which is substituted by E and/or interrupted by D; $C_5$-$C_{12}$cycloalkyl, $C_5$-$C_{12}$cycloalkyl, which is substituted by E and/or interrupted by D; $C_6$-$C_{18}$aryl; $C_6$-$C_{18}$aryl, which is substituted by G; $C_2$-$C_{18}$heteroaryl; $C_2$-$C_{18}$heteroaryl, which is substituted by G;

if n is 2, L is —OCO—O—.

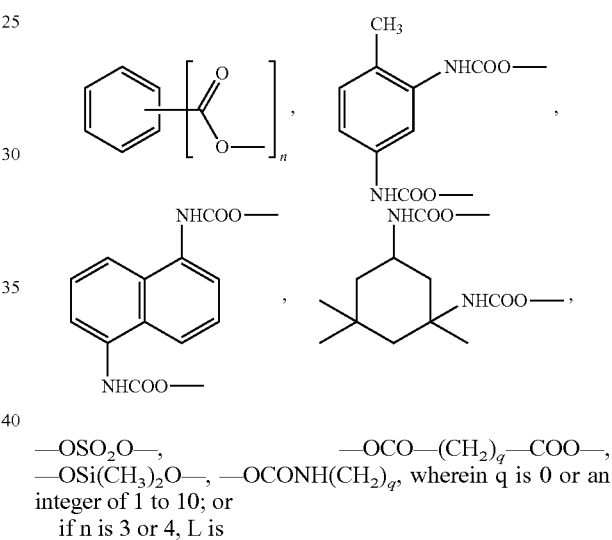

—$OSO_2O$—, —$OCO$—$(CH_2)_q$—$COO$—, —$OSi(CH_3)_2O$—, —$OCONH(CH_2)_q$, wherein q is 0 or an integer of 1 to 10; or if n is 3 or 4, L is

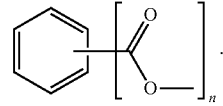

In the definitions, the ring system formed by $R^1$ together with the carbon and nitrogen atom, it is linked to, corresponding to

is a mono- or polycyclic $C_2$-$C_{20}$ ring system, which, in addition to the N may contain one or more heteroatoms of O, S and/or N and/or may be unsubstituted or substituted, as specified in claim 1.

The ring system may be an aromatic or non-aromatic heterocyclic system.

Preferably, the $C_2$-$C_{20}$ ring system comprises 1 to 4 annellated rings and up to 5 heteroatoms selected from O, N and/or S. More preferred, the $C_2$-$C_{20}$ ring system comprises 1 to 3, for example 1 or 2, annellated rings and 1 to 3, for example 1 or 2, heteroatoms selected from N and/or S.

Alkyl groups may be within the given limits of carbon atoms linear or branched, where possible. Examples are methyl, ethyl, n-propyl, isopropyl, n-butyl, sec-butyl, isobutyl, tert-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, octadecyl.

Cycloalkyl groups may be within the given limits, for example, cyclopentyl, cyclohexyl, cycloheptyl, cyclooctyl, methylcyclopentyl, dimethylcyclopentyl, methylcyclohexyl and dimethylcyclohexyl, preferably cyclohexyl. The cycloalkyl group, in particular a cyclohexyl group, may be condensed one or twice by phenyl which may be substituted one to three times with $C_1$-$C_4$alkyl and halogen.

Cycloalkenyl groups may be within the given limits, for example, cyclopentenyl, cyclohexenyl, methylcyclopentenyl, dimethylcyclopentenyl and methylcyclohexenyl. Cycloalkenyl may comprise more than one double bond that may be conjugated or non-conjugated, for example may comprise one double bond.

Alkenyl groups may be within the given limits of carbon atoms straight-chain or branched, where possible. Examples are vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, oleyl, n-dodec-2-enyl or n-octadec-4-enyl. The term alkenyl also comprises residues with more than one double bond that may be conjugated or non-conjugated, for example may comprise one double bond.

Alkynyl groups may be within the given limits of carbon atoms straight-chain or branched, where possible. Examples are ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl or 1-decyn-10-yl. The term alkynyl also comprises residues with more than one triple bond and residues with a triple bond and a double bond, all of which may be conjugated or non-conjugated. For instance, alkynyl comprises one triple bond.

The term "aryl group" is typically $C_6$-$C_{18}$aryl, such as phenyl, indenyl, azulenyl, naphthyl, biphenyl or terphenylyl, as-indacenyl, s-indacenyl, acenaphthylenyl, phenanthryl, fluoranthenyl, triphenylenyl, chrysenyl, naphthacen, picenyl, perylenyl, pentaphenyl, hexacenyl, pyrenyl, or anthracenyl, preferably phenyl, 1-naphthyl, 2-naphthyl, 9-phenanthryl, 2- or 9-fluorenyl, 3- or 4-biphenyl.

Alkoxy groups may be within the given limits of carbon atoms straight-chain or branched alkoxy groups, e.g. methoxy, ethoxy, n-propoxy, isopropoxy, n-butoxy, sec-butoxy, isobutoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy.

The term "alkylthio group" means the same groups as the alkoxy groups, except that the oxygen atom of the ether linkage is replaced by a sulfur atom.

Aralkyl groups may be within the given limits of carbon atoms, for example, benzyl, 2-benzyl-2-propyl, β-phenyl-ethyl (phenethyl), α,α-dimethylbenzyl, ω-phenyl-butyl, ω,ω-dimethyl-co-phenyl-butyl, ω-phenyl-dodecyl, in which both the aliphatic and the aromatic hydrocarbon group may be unsubstituted or substituted. Preferred examples are benzyl, phenethyl and α,α-dimethylbenzyl.

The term "heteroaryl group", especially $C_2$-$C_{18}$heteroaryl, is a ring, wherein nitrogen, oxygen or sulfur are the possible hetero atoms, and is typically an unsaturated heterocyclic radical with five to 18 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, 2H-chromenyl, xanthenyl, dibenzofuranyl, phenoxythienyl, pyrrolyl, imidazolyl, pyrazolyl, pyridyl, bipyridyl, triazinyl, pyrimidinyl, pyrazinyl, 1H-pyrrolizinyl, isoindolyl, pyridazinyl, indolizinyl, isoindolyl, indolyl, 3H-indolyl, phthalazinyl, naphthyridinyl, quinoxalinyl, quinazolinyl, cinnolinyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, 4aH-carbazolyl, carbolinyl, benzotriazolyl, benzoxazolyl, phenanthridinyl, acridinyl, perimidinyl, phenanthrolinyl, phenazinyl, isothiazolyl, phenothiazinyl, isoxazolyl, furazanyl or phenoxazinyl.

Halogen denotes I, Br, Cl, F, especially, Br or Cl.

Examples of a 5 to 12 membered ring formed by $R^2$ and $R^3$, $R^4$ and $R^5$, $R^2$ and $R^4$ or two of $R^5$ are cycloalkanes which may have one additional hetero atom selected from NR', O and S, wherein R' is $C_1$-$C_{18}$alkyl or phenyl, and/or said ring may be substituted by E and/or interrupted by D. Preferred are 5 to 7 membered cycloalkanes.

Examples of a 5 to 7 membered ring formed by $R^7$ and $R^8$, $R^9$ and $R^{10}$, $R^{16}$ and $R^{17}$, $R^{19}$ and $R^{20}$, $R^{31}$ and $R^{32}$, $R^{35}$ and $R^{36}$, or $R^{42}$ and $R^{43}$ are heterocycloalkanes or heterocycloalkenes having 3 to 6 carbon atoms and optionally one additional hetero atom selected from NR', O and S, wherein R' is $C_1$-$C_{18}$alkyl or phenyl; said 5 to 7 membered ring may be substituted by E and/or interrupted by D.

Examples are

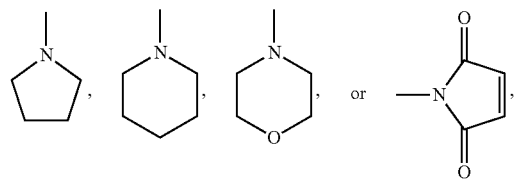

which may be part of a bicyclic system, for example

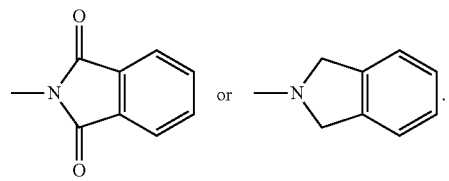

Examples of a 5 to 7 membered ring formed by two of $R^{45}$ are heterocycloalkanes or heterocycloalkenes having from 3 to 6 carbon atoms, for example,

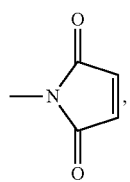

which may be part of a bicyclic system, for example

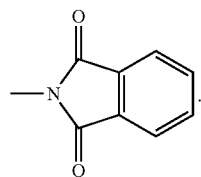

The term "in each occurrence" for $R^4$ and $R^5$ means that the radicals $R^4$ and $R^5$ may have independently from each other different meanings, if p is 2, 3 or 4.

As described above, the aforementioned radicals may be substituted by E and/or, if desired, interrupted by D. Interruptions are of course possible only in the case of radicals containing at least 2 carbon atoms connected to one another by single bonds; $C_6$-$C_{18}$aryl is not interrupted; interrupted arylalkyl or alkylaryl contains the unit D in the alkyl moiety. $C_1$-$C_{18}$alkyl substituted by one or more E and/or interrupted by one or more units D is, for example, $(CH_2CH_2O)_s$—$R^x$, wherein s is a number from the range 1-9 and $R^x$ is H or $C_1$-$C_{10}$alkyl or $C_2$-$C_{10}$alkanoyl (e.g. CO—CH($C_2H_5$)$C_4H_9$), $CH_2$—CH(OR$^{y'}$)—$CH_2$—O—$R^y$, where $R^y$ is $C_1$-$C_{18}$alkyl, $C_5$-$C_{12}$cycloalkyl, phenyl, $C_7$-$C_{15}$phenylalkyl, and $R^{y'}$ embraces the same definitions as $R^y$ or is H; $C_1$-$C_8$alkylene-COO—$R^z$, e.g. $CH_2COOR^z$, $CH(CH_3)COOR^z$, $C(CH_3)_2$CO-O$R^z$, wherein $R^z$ is H, $C_1$-$C_{18}$alkyl, $(CH_2CH_2O)_{1-9}$—$R^x$, and $R^x$ embraces the definitions indicated above; $CH_2CH_2$—O—CO—CH=$CH_2$; $CH_2CH(OH)CH_2$—O—CO—C($CH_3$)=$CH_2$.

The term "substituted by G" means that one, or more, especially one to three substituents G might be present.

The term "at least" is intended to define one or more than, e.g. one or two or three, preferably one or two.

In another preferred embodiment the curable composition comprises as a component (B) a compound of formula (I), wherein $R^2$, $R^3$, $R^4$ and $R^5$ are independently of each other H; $C_1$-$C_8$alkyl; $C_5$-$C_8$cycloalkyl; $C_6$-$C_{18}$aryl; $C_6$-$C_{18}$aryl, which is substituted by G; $C_2$-$C_{18}$heteroaryl; $C_2$-$C_{18}$heteroaryl, which is substituted by G; $C_1$-$C_4$alkoxy; $C_7$-$C_{10}$aralkyl; $NHR^6$, $NR^7R^8$, wherein $R^6$, $R^7$ and $R^8$ are independently of each other $C_1$-$C_4$alkyl; $C_6$-$C_{12}$aryl; $C_6$-$C_{12}$aryl, which is substituted by $C_1$-$C_4$alkyl or $C_1$-$C_4$alkoxy; $C_7$-$C_{10}$aralkyl; or $R^7$ and $R^8$ form an organic bridging group completing, together with the nitrogen atom, they are linked to, a heterocyclic ring of 5 to 7 ring atoms in total;

or $R^2$ and $R^3$, $R^4$ and $R^5$, or $R^2$ and $R^4$ form an organic bridging group completing, together with the carbon atom, they are linked to, a carbocyclic or heterocyclic ring of 5 to 7 ring atoms in total;

or two of $R^5$, which are linked to adjacent carbon atoms, form an organic bridging group completing, together with the carbon atom, they are linked to, a carbocyclic or heterocyclic ring of 5 to 7 ring atoms in total;

Preferably, the composition comprises as a component (B) a compound of formula (I), wherein $R^2$, $R^3$, $R^4$ and $R^5$ are independently of each other H or $C_1$-$C_4$alkyl, and p is an integer of 1 or 2.

In another preferred embodiment the invention relates to compositions comprising as a component (B) a compound of formula (I), wherein $R^1$ forms together with the carbon and nitrogen atom, it is linked to, a mono- or polycyclic $C_2$-$C_{20}$ ring system selected from the group consisting of imidazole, benzimidazole, thiazole, benzothiazole, pyrazole, oxazole, benzoxazole, isoxazole, isothiazole, 1,2,3-triazole, 1,2,4-triazole, tetrazole, 1,2,4-oxadiazole, 1,2,4-thiadiazole, 1,3,4-oxadiazole, 1,3,4-thiadiazole, pyridine, quinoline, isoquinoline, phenanthridine, pyridazine, pyrimidine, pyrazine, cinnoline, phthalazine, chinazoline, chinoxaline, chinazolinone, 1,3,5-triazine, 1,2,4,5-tetrazine, purine, xanthine, hypoxanthine, guanine, adenine, pteridine, pterine, 1,10-phenanthroline, 2,2'-bipyridine, 4,4'-bipyridine,

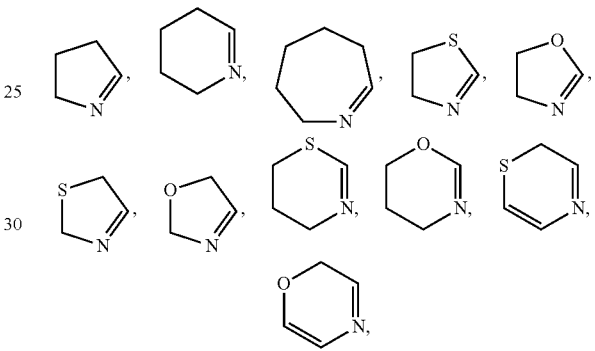

said ring system is unsubstituted or substituted by $C_1$-$C_8$alkyl; $C_5$-$C_7$cycloalkyl; $C_6$-$C_{12}$aryl; $C_6$-$C_{18}$aryl, which is substituted by G; $C_2$-$C_{18}$heteroaryl; $C_2$-$C_{18}$heteroaryl, which is substituted by G; $C_1$-$C_8$alkoxy; $C_1$-$C_8$alkoxy, which is substituted by E and/or interrupted by D; $C_7$-$C_{11}$aralkyl; $C_7$-$C_{11}$aralkyl, which is substituted by G;

halogen, OH, oxo, CN, $NH_2$, $NHR^6$, $NR^7R^8$, $CONH_2$, $CONR^9R^{10}$, $COR^{11}$, C(O)O$R^{12}$, wherein $R^6$, $R^7$, $R^8$, $R^9$, $R^{10}$, $R^{11}$ and $R^{12}$ are independently of each other $C_1$-$C_8$alkyl; $C_1$-$C_8$alkyl, which is interrupted by —O—; $C_6$-$C_{12}$aryl; $C_6$-$C_{12}$aryl, which is substituted by $C_1$-$C_8$alkyl or $C_1$-$C_8$alkoxy; $C_7$-$C_{11}$aralkyl; $C_7$-$C_{11}$aralkyl, which is substituted by G;

or $R^7$ and $R^8$ form an organic bridging group completing, together with the nitrogen atom, they are linked to, a heterocyclic ring of 5 to 7 ring atoms in total;

or said ring system is further anellated by one or more benzene rings.

More preferred are compositions comprising as a component (B) a compound of formula (I), wherein $R^1$ forms together with the carbon and nitrogen atom, it is linked to, a mono- or polycyclic $C_1$-$C_{20}$ ring system selected from the group consisting of imidazole, benzimidazole, thiazole, benzothiazole, oxazole, benzoxazole, isothiazole, pyridine, chinoline, isochinoline, phenanthridine, pyridazine, pyrimidine, pyrazine, cinnoline, phthalazine, chinazoline, chinoxaline, purine, 1,10-phenanthroline, 2,2'-bipyridine and 4,4'-bipyridine;

said ring system is unsubstituted or substituted by $C_1$-$C_4$alkyl; phenyl; phenyl, which is substituted by $C_1$-$C_4$alkyl, $C_1$-$C_4$alkoxy or halogen; $C_1$-$C_4$alkoxy; benzyl; phenethyl; halogen, OH, $NH_2$, $NHR^6$, $NR^7R^8$, $CONH_2$, $CONR^9R^{10}$, $COR^{11}$, $C(O)OR^{12}$, wherein $R^6$, $R^7$, $R^8$, $R^9$, $R^{10}$, $R^{11}$ and $R^{12}$ are independently of each other $C_1$-$C_4$alkyl; phenyl; benzyl; phenethyl;

or $R^7$ and $R^8$ form an organic bridging group completing, together with the nitrogen atom, they are linked to, a heterocyclic ring of 5 to 6 ring atoms in total;

or said ring system is further anellated by one or more benzene rings.

In another preferred embodiment the invention relates to compositions comprising as a component (B) a compound of formula (I), wherein n is 1 and L is halogen, OH, $OR^{40}$, $SR^{40}$, $OCOR^{40}$, $OCOOR^{41}$, $OCONR^{42}R^{43}$, $OCSNR^{42}R^{43}$, $NR^{42}R^{43}$, wherein $R^{40}$, $R^{42}$, $R^{43}$ are independently of each other H, $C_1$-$C_8$alkyl; phenyl; or benzyl.

Particularly preferred are compositions comprising as a component (B) a compound of formula (I), wherein n is 1 and L is halogen, OH, OMe, SMe, $NH_2$, $NMe_2$, OCOMe, OCOPh, OCOtBu, $OCSNMe_2$, $OCONMe_2$, OCONHMe, OCONHEt, OCONHPh, OCOOMe, OCOOtBu, OCOOPh, $OCOOCH_2Ph$.

Examples of particular suitable thermolatent bases include

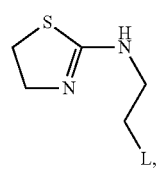 (I-12)

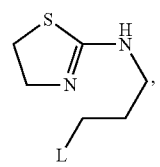 (I-13)

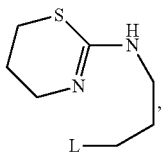 (I-14)

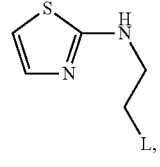 (I-15)

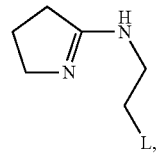 (I-16)

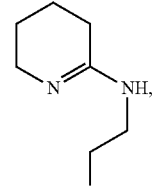 (I-17)

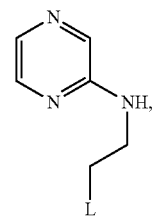 (I-18)

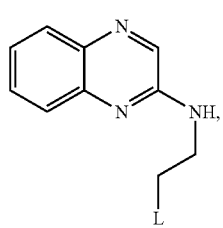 (I-19)

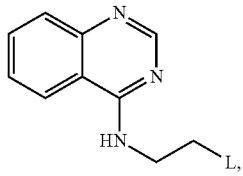 (I-20)

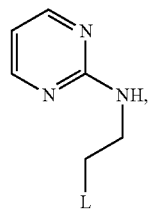 (I-21)

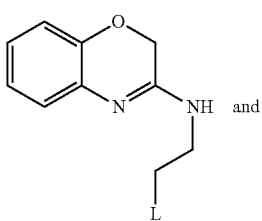 (I-22) and

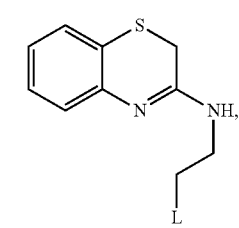 (I-23)

wherein L is as defined above, preferably halogen, OH, OMe, SMe, NH$_2$, NMe$_2$, OCOMe, OCOPh, OCOtBu, OCSNMe$_2$, OCONMe$_2$, OCONHMe, OCONHEt, OCONHPh, OCOOMe, OCOOtBu, OCOOPh, OCOOCH$_2$Ph.

Examples of thermolatent bases, wherein the mono- or polycyclic C$_2$-C$_{20}$ ring system is substituted by one or more groups of formula

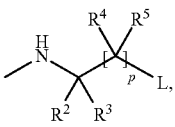 (II)

wherein R$^2$, R$^3$, R$^4$, R$^5$, L and p are defined, as above, include (II-1)

and

-continued

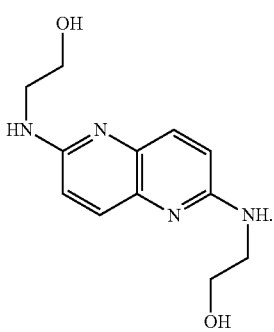

(II-2)

The transformation of a weak thermolatent base, a compound of formula (I), into the released or activated base, a compound of formula (V), according to the aforementioned reaction scheme is accompanied by an increase of basicity. Generally, the compounds of formula (V) have a pKa value of from 6 to 15, preferably of from 8 to 15, and the change of pKa during the transformation is about 2 to 8.

For example, the increase of basicity may be demonstrated with pKa data calculated using the Advanced Chemistry Development (ACD/Labs) Software V8.14 for Solaris, as shown in Table 1.

TABLE 1

| Thermolatent base | Released base |
|---|---|
| pKA = 5.93 ± 0.19 | pKA = 12.5 ± 0.50 |
| pKA = 6.20 ± 0.19 | pKA = 10.44 ± 0.20 |
| pKA = 4.85 ± 0.61 | pKA = 10.91 ± 0.20 |
| pKA = 5.73 ± 0.50 | pKA = 10.78 ± 0.20 |

TABLE 1-continued

| Thermolatent base | Released base |
|---|---|
| pKA = 2.26 ± 0.23 | pKA = 9.30 ± 0.50 |
| pKA = 3.84 ± 0.12 | pKA = 10.10 ± 0.50 |

Component (A), i.e. the organic material which is polymerisable or crosslinkable with basic or nucleophilic catalyst, may generally be in the form of mono- or polyfunctional monomers, oligomers or polymers. Particularly preferred oligomeric/polymeric systems are binders or coating systems as are customary in the coatings industry.

Accordingly, in another preferred embodiment the present invention is directed to a curable composition, wherein component (A) is one of the following systems:

a) acrylate copolymers having alkoxysilane or alkoxysiloxane side groups, for example the polymers described in U.S. Pat. No. 4,772,672 or U.S. Pat. No. 4,444,974;

b) two-component systems comprising hydroxyl group-containing polyacrylates, polyesters and/or polyethers and aliphatic or aromatic polyisocyanates;

c) two-component systems comprising functional polyacrylates and/or polyesters and a polyepoxide, where the polyacrylate and/or the polyester contain(s) carboxyl or anhydride groups;

d) two-component systems comprising fluorine-modified or silicone-modified hydroxyl group-containing polyacrylates, polyesters and/or polyethers and aliphatic or aromatic polyisocyanates;

e) two-component systems comprising (poly)ketimines and aliphatic or aromatic polyisocyanates;

f) two-component systems comprising (poly)ketimines and unsaturated acrylate resins or acetoacetate resins or methyl α-acrylamidomethylglycolate;

h) two-component systems comprising (poly)oxazolidines and polyacrylates containing anhydride groups, or unsaturated acrylate resins or polyisocyanates;

i) two-component systems comprising epoxy-containing polyacrylates and carboxyl-group containing polyacrylates or a dicarboxylic acid, e.g. dodecanediacid;

l) polymers based on allyl glycidyl ether;

m) two-component systems comprising a (poly)alcohol and a (poly)isocyanate;

n) two-component systems comprising an α,β-ethylenically unsaturated carbonyl compound and a polymer which contains activated $CH_2$ groups, it being possible for the activated $CH_2$ groups to be present either in the main chain or in the side chain or in both, as is described, for example, in EP-B-0 161 697 for (poly)malonate groups. Other compounds having activated $CH_2$ groups are (poly)acetoacetates and (poly)cyanoacetates.

Among these base-catalysable binders particular preference is given to the following:

b) two-component systems comprising hydroxyl group-containing polyacrylates, polyesters and/or polyethers and aliphatic or aromatic polyisocyanates;

c) two-component systems comprising functional polyacrylates and/or polyesters and a polyepoxide, where the polyacrylate and/or the polyester contain(s) carboxyl or anhydride groups;

i) two-component systems comprising epoxy-containing polyacrylates and carboxyl-group containing polyacrylates or a dicarboxylic acid, e.g. dodecanediacid;

m) two-component systems comprising a (poly)alcohol and a (poly)isocyanate, and n) two-component systems comprising an α,β-ethylenically unsaturated carbonyl compound and a polymer which contains activated $CH_2$ groups, it being possible for the activated $CH_2$ groups to be present either in the main chain or in the side chain or in both, as is described, for example, in EP-B-0 161 697 for (poly)malonate groups. Other compounds having activated $CH_2$ groups are (poly)acetoacetates and (poly)cyanoacetates.

Two-component systems comprising an α,β-ethylenically unsaturated carbonyl compound and a (poly)malonate, and their preparation, are described in EP-B-0 161 697. The malonate group here can be attached in a polyurethane, polyester, polyacrylate, epoxy resin, poly-amide or polyvinyl polymer either in the main chain or in a side chain. The α,β-ethylenically unsaturated carbonyl compound employed can be any double bond activated by a carbonyl group. Examples are esters or amides of acrylic acid or methacrylic acid. In the ester groups it is also possible for additional hydroxyl groups to be present. Diesters and triesters are also possible.

Typical examples are hexanediol diacrylate or trimethylolpropane triacrylate. Instead of the acrylic acid it is also possible to use other acids and their esters or amides, such as crotonic or cinnamic acid.

Under base catalysis, the components of the system react with one another to form a crosslinked coating system which is suitable for numerous applications. Owing to its good inherent weathering resistance it is suitable, for example, for exterior applications as well and can, if required, be additionally stabilised by UV absorbers and other light stabilisers.

Mixtures of the above-mentioned systems are also possible.

Other systems suitable as a component (A) in the novel compositions are epoxy systems. Epoxy resins are suitable for preparing novel, curable mixtures comprising epoxy resins as component (A) are those which are customary in epoxy resin technology, examples of such epoxy resins being:

I) Polyglycidyl and poly(β-methylglycidyl) esters, obtainable by reacting a compound having at least two carboxyl groups in the molecule with epichlorohydrin or β-methylepichlorohydrin. The reaction is judiciously carried out in the presence of bases. As the compound having at least two carboxyl groups in the molecule it is possible to use aliphatic polycarboxylic acids. Examples of such polycarboxylic acids are oxalic, succinic, glutaric, adipic, pimelic, suberic, azelaic or dimerised or trimerised linoleic acid. It is also possible, however, to employ cyclo-aliphatic polycarboxylic acids, such as tetrahydrophthalic, 4-methyltetrahydrophthalic, hexa-hydrophthalic or 4-methylhexahydrophthalic acid. Aromatic polycarboxylic acids, furthermore, can be used, such as phthalic, isophthalic or terephthalic acid.

II) Polyglycidyl or poly(β-methylglycidyl) ethers, obtainable by reacting a compound having at least two free alcoholic hydroxyl groups and/or phenolic hydroxyl groups with epichloro-hydrin or β-methylepichlorohydrin under alkaline conditions or in the presence of an acidic catalyst with subsequent alkali treatment.

The glycidyl ethers of this type are derived, for example, from acyclic alcohols, such as ethylene glycol, diethylene glycol and higher poly(oxyethylene) glycols, propane-1,2-diol or poly(oxypropylene) glycols, propane-1,3-diol, butane-1,4-diol, poly(oxytetramethylene)glycols, pentane-1,5-diol, hexane-1,6-diol, hexane-2,4,6-triol, glycerol, 1,1,1-trimethylolpropane, pentaerythritol, sorbitol, and from poly-epichlorohydrins. They also derive, for example, from cycloaliphatic alcohols, such as 1,4-cyclohexanedimethanol, bis(4-hydroxycyclohexyl)-methane or 2,2-bis(4-hydroxycyclohexyl)propane, or possess aromatic nuclei, such as N,N-bis(2-hydroxyethyl)aniline or p,p'-bis(2-hydroxyethylamino)diphenylmethane. The glycidyl ethers can also be derived from mononuclear phenols, such as resorcinol or hydroquinone, or are based on polynuclear phenols, such as bis(4-hydroxyphenyl)methane, 4,4'-dihydroxy-biphenyl, bis(4-hydroxyphenyl) sulfone, 1,1,2,2-tetrakis(4-hydroxyphenyl)ethane, 2,2-bis(4-hydroxyphenyl)propane, 2,2-bis(3,5-dibromo-4-hydroxyphenyl)propane and from novolaks, obtainable by condensing aldehydes, such as formaldehyde, acetaldehyde, chloral or furfuraldehyde, with phenols, such as phenol, or with phenols whose nucleus is substituted by chlorine atoms or $C_1$-$C_9$alkyl groups, examples being 4-chlorophenol, 2-methylphenol, or 4-tert-butylphenol, or by condensation with bisphenols, those of the type specified above.

III) Poly(N-glycidyl) compounds, obtainable by dehydrochlorination of the reaction products of epichlorohydrin with amines containing at least two active hydrogen bound to amino nitrogen atoms. These amines are, for example, aniline, n-butylamine, bis(4-aminophenyl)-methane, m-xylylenediamine or bis(4-methylaminophenyl)methane.

The poly(N-glycidyl) compounds also include triglycidyl isocyanurate, N,N'-diglycidyl derivatives of cycloalkylene ureas, such as ethylene urea or 1,3-propylene urea, and diglycidyl derivatives of hydantoins, such as of 5,5-dimethylhydantoin.

IV) Poly(S-glycidyl) compounds, for example di-S-glycidyl derivatives derived from dithiols such as ethane-1,2-dithiol or bis(4-mercaptomethylphenyl) ether.

V) Cycloaliphatic epoxy resins, for example bis(2,3-epoxycyclopentyl) ether, 2,3-epoxy-cyclopentyl glycidyl ether, 1,2-bis(2,3-epoxycyclopentyloxy)ethane or 3,4-epoxycyclohexyl-methyl 3',4'-epoxycyclohexanecarboxylate.

However, it is also possible to use epoxy resins in which the 1,2-epoxide groups are attached to different heteroatoms and/or functional groups; these compounds include, for example, the N,N,O-triglycidyl derivative of 4-aminophenol, the glycidyl ether glycidyl ester of salicylic acid, N-glycidyl-N'-(2-glycidyloxypropyl)-5,5-dimethylhydantoin or 2-glycidyloxy-1,3-bis(5,5-dimethyl-1-glycidylhydantoin-3-yl) propane.

Mixtures of epoxy resins may also be used as component (A).

Accordingly, in another preferred embodiment, the present invention is directed to a composition, wherein component (A) is an epoxy resin or a mixture of different epoxy resins.

Typically, the thermolatent base may be used in the curable composition according to the present invention in an amount of from 0.01 to 15% by weight, preferably from 0.1 to 10% by weight and more preferably from 0.1 to 2% by weight, based on the weight of component (A).

The component (B), i.e. the thermolatent base, may be used alone or as a combination of two or more of them. Further, they may be used together with known thermolatent bases as a combination. Examples of known thermolatent bases have been described in the documents mentioned in the prior art.

Suitable examples of thermolatent bases may be N-alkoxycarbonyl imidazoles, as described in WO 98/04531, such as

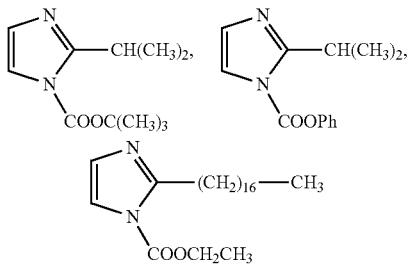

or imidazole derivatives described in U.S. Pat. No. 5,623,023.

Further, a photolatent base may be added to the curable composition of the invention.

Examples of photolatent bases are capped amine compounds, for example compounds of the classes: o-nitrobenzyloxycarbonylamines, 3,5-dimethoxy-α,α-dimethylbenzyloxycarbonyl-amines, benzoin carbamates, derivatives of anilides, photolatent guanidines, generally photolatent tertiary amines, for example ammonium salts of ketocarboxylic acids, or other carboxylates, benzhydrylammonium salts, N-(benzophenonylmethyl)-tri-N-alkylammonium triphenylalkyl borates, photolatent bases based on metal complexes, e.g. cobalt amine complexes, tungsten and chromium pyridinium pentacarbonyl complexes, anion-generating photoinitiators based on metals, such as chromium and cobalt complexes "Reinecke salts" or metalloporphyrins. Examples thereof are published in J. V. Crivello, K. Dietliker "Photoinitiators for Free Radical, Cationic & Anionic Photopolymerisation", Vol. III of "Chemistry & Technology of UV & EB Formulation for Coatings, Inks & Paints", 2nd Ed., J. Wiley and Sons/SITA Technology (London), 1998 or in WO 98/32756, WO 98/38195, WO 98/41524 and WO 00/10964.

Also suitable as photolatent base catalyst for the compositions according to the invention are bases as described in WO 97/31033. They are especially latent bases based on secondary amines, guanidines or amidines. Also suitable as photolatent base donors are the α-aminoketone compounds described in EP-A-0 898 202, for example (4-morpholinobenzoyl)-1-benzyl-1-dimethylamino-propane or (4-methylthiobenzoyl)-1-methyl-1-morpholino-ethane. Further interesting photolatent base compounds are of the following structure

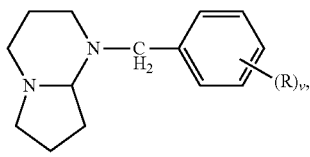

for example disclosed in WO 03/33500.

The photolatent bases may be generally present in an amount of from 0 to 10% by weight, preferably from 0.01 to 10% by weight and more preferably from 0.01 to 2% by weight, based on the weight of component (A).

Optionally, the thermolatent base may be used in combination with a further curing catalyst, referred to as component (C), for example another base. Suitable examples are aromatic amines, such as imidazole or substituted imidazoles, e.g. 2-methylimidazole, or pyridine, aliphatic amines, such as 2,2,6,6-tetramethylpiperidine, morpholine, piperazine or piperidine, or amidines, such as 1,5-diazabicyclo[4.3.0]non-5-ene (DBN), 1,8-diazabicyclo[5.4.0]undec-7-ene (DBU) or 1,4-diazabicyclo[2.2.2]octane (DABCO), or mixtures thereof.

The additional curing catalyst may be present in the curable composition of the invention in an amount of from 0 to 1% by weight, preferably from 0.5 to 1% by weight, based on the weight of component (A).

In general, the curable composition of the invention may include, as further additives, i.e. component (D), one or more compounds of the group of the pigments, dyes, fillers, waxes, levelling agents, degassing agents, charge control agents, optical brighteners, adhesion promoters, antioxidants, light stabilizers, plasticizers, rheologic and thixotropic agents or photoinitiators. The composition may also include corrosion inhibitors, for example anticorrosion pigments, such as phosphate- or borate-containing pigments or metal oxide pigments, or other organic or inorganic corrosion inhibitors, for example salts of nitroisophthalic acid, phosphoric esters, technical-grade amines or substituted benzotriazoles. The additional additives may usually be added in an amount of from 0 to 20% by weight, preferably of from 0.1 to 15% by weight, based on the weight of component (A).

Accordingly, in a preferred embodiment the invention is directed to a curable composition further comprising (C) a curing catalyst other than component (B) and
(D) at least one additive.

In a more preferred embodiment the invention is directed to a curable composition further comprising (C) a curing catalyst other than component (B) and
(D) at least one additive selected from the group consisting of pigments, dyes, fillers, waxes, stabilizers, levelling agents, rheologic and thixotropic agents, degassing agents, charge control agents, optical brighteners, adhesion promoters, flameproofing agents and plasticizers.

Examples for additional additives are given below.

1. Antioxidants 1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctyl-thiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxy-phenol, 2,5-di-tert-butylhydroquinone, 2,5-di-tert-amylhydroquinone, 2,6-diphenyl-4-octade-cyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl)adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)-disulfide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butyl-phenol), 2,2'-ethylidenebis(6-tert-butyl-4-isobutylphenol), 2,2'-methylenebis [6-(α-methyl-benzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxy-benzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)-dicyclopentadiene, bis[2-(3'-tert-butyl-2'-hydroxy-5'-methyl-benzyl)-6-tert-butyl-4-methyl-phenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecyl-mercaptobutane, 1,1,5,5-tetra(5-tert-butyl-4-hydroxy-2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-di methyl benzylmercaptoacetate, tridecyl-4-hydroxy-3,5-d i-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxy-benzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, didodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl) malonate.

1.9. Aromatic hydroxybenzyl compounds, for example 1,3,5-tris-(3,5-di-tert-butyl-4-hydroxy-benzyl)-2,4,6-trimethylbenzene, 1,4-bis(3,5-di-tert-butyl-4-hydroxybenzyl)-2,3,5,6-tetra-methylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxy-anilino)-1,3,5-triazine, 2-octylmercapto-4,6-bis(3,5-di-tert-butyl-4-hydroxyanilino)-1,3,5-tri-azine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris-(3,5-di-tert-butyl-4-hydroxybenzyl)isocyanurate 1,3,5-tris(4-tert-butyl-3-hydroxy-2,6-dimethylbenzyl)isocyanurate, 2,4,6-tris-(3,5-di-tert-butyl-4-hydroxyphenylethyl)-1,3,5-triazine, 1,3,5-tris(3,5-di-tert-butyl-4-hydroxy-phenylpropionyl 1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-d i-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of 13-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.14. Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]-undecane.

1.15. Esters of β-(3-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, tri-ethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxy-phenylpropionyl)trimethylenediamide, N,N'-bis(3,5-di-tert-butyl-4-hydroxyphenylpropionyl)-hydrazide, N,N'-bis[2-(3-[3,5-di-tert-butyl-4-hydroxyphenyl] propionyloxy)ethyl]oxamide (Naugard®XL-1, supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenyl-amine, N-phenyl-1- naphthylamine, N-(4-tert-octylphenyl)-1-naphthylamine, N-phenyl-2-naphthylamine, octylated diphenylamine, for example p,p'-di-tert-octyldiphenylamine, 4-n-butyl-aminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylamino-methylphenol, 2,4'-diaminodiphenylmethane, 4,4'-diaminodiphenylmethane, N,N,N',N'-tetra-methyl-4,4'-diaminodiphenylmethane, 1,2-bis[(2-methylphenyl)amino]ethane, 1,2-bis(phenyl-amino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenyl-amines, a mixture of mono- and dialkylated nonyldiphenylamines, a mixture of mono- and dialkylated dodecyldiphenylamines, a mixture of mono- and dialkylated isopropyl/isohexyl-diphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octyl-phenothiazines, N-allylphenothiazine, N,N,N',N'-tetraphenyl-1,4-diaminobut-2-ene, N,N-bis(2,2,6,6-tetramethylpiperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV absorbers and light stabilisers 2.1. 2-(2'-Hydroxyphenyl)benzotriazoles, for example 2-(2'-hydroxy-5'-methylphenyl)-benzo-triazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5-ditert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-2-methoxycarbonylethyl)phenyl)-5-chloro-benzotriazole, 2-(3'-tert-butyl-2'-hydroxy-5'-(2-meth-oxycarbonylethyl)phenyl)benzotriazole, 2-(3'-tert-butyl-2'-hydroxy-5'-(2-octyloxycarbonyl-ethyl)phenyl)benzotriazole, 2-(3'-tert-butyl-5'-[2-(2-ethylhexyloxy)carbonylethyl]-2'-hydroxy-phenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 330;

where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]-benzotriazole; 2-[2'-hydroxy-3'-(1,1,3,3-tetramethylbutyl)-5'-(α,α-dimethylbenzyl)-phenyl]benzotriazole.

2.2. 2-Hydroxybenzophenones, for example the 4-hydroxy, 4-methoxy, 4-octyloxy, 4-decyl-oxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butyl-phenyl salicylate, phenyl salicylate, octylphenyl salicylate, dibenzoyl resorcinol, bis(4-tert-butyl-benzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethyl-butyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl-undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-di-chloro-1,3,5-triazine, tris(2,2,6,6-tetramethyl-4-piperidyl)nitrilotriacetate, tetrakis(2,2,6,6-tetra-methyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethyl-piperidine, bis(1,2,2,6,6-pentamethylpiperidyl)-2-n-butyl-2-(2-hydroxy-3,5-di-tert-butylbenzyl)-malonate, 3-n-octyl-7,7,9,9-tetramethyl-1,3,8-triazaspiro[4.5]decane-2,4-dione, bis(1-octyl-oxy-2,2,6,6-tetramethylpiperidyl)sebacate, bis(1-octyloxy-2,2,6,6-tetramethylpiperidyl)succinate, linear or cyclic condensates of N,N'-bis-(2,2,6,6-tetramethyl-4-piperidyl)hexamethyl-enediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxospiro[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl)hexa-methylenediamine, a diester of 4-methoxy-methylene-malonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-henyl]-4,6-bis(2,4-dimethylphenyl)-1,3,5-triazine, 2-[2-hydroxy-4-(2-hydroxy-3-dodecyloxy-ropoxy)phenyl]-4,6-bis(2,4-dimethyl-phenyl)-, 3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-ropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyldihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris (2,4-di-tert-butylphenyl) phosphite, diisodecyl pentaerythritol diphosphite, bis(2,4-di-tert-butylphenyl) pentaerythritol diphosphite, bis(2,4-di-cumylphenyl)pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)-pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2', 2"-nitrilo-[triethyltris(3,3',5,5'-tetra-tert-butyl-1,1'-biphenyl-2,2'-diyl)phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

The following phosphites are especially preferred:
Tris(2,4-di-tert-butylphenyl) phosphite (Irgafos 168, Ciba-Geigy), tris(nonylphenyl) phosphite,

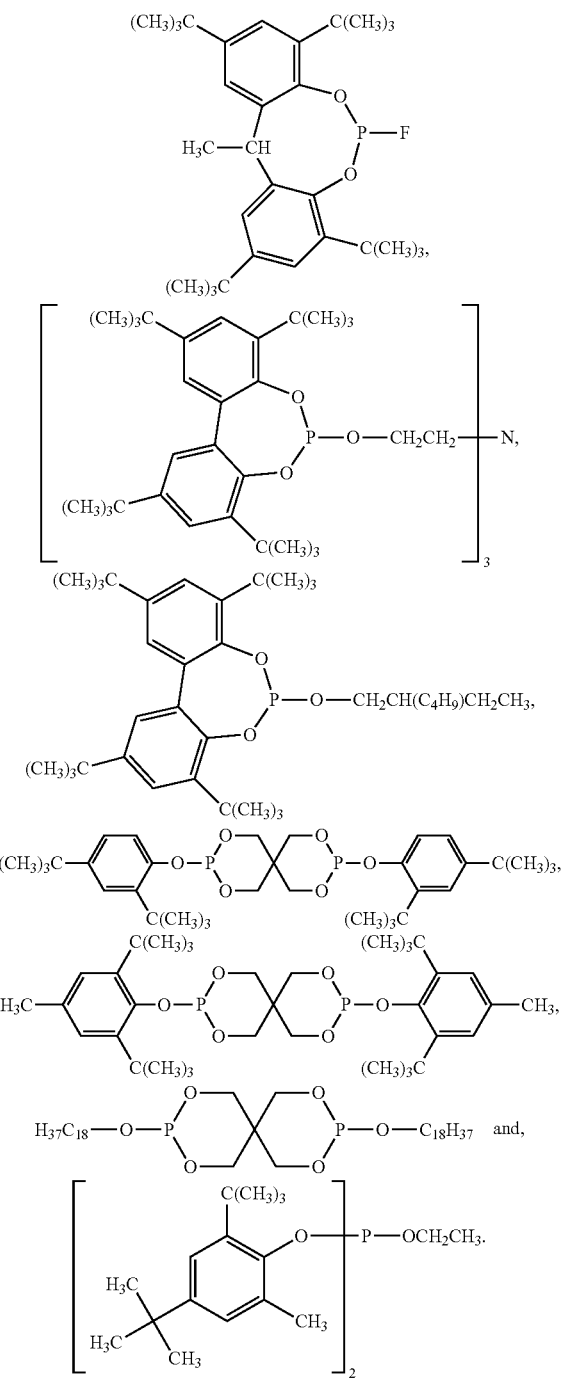

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydrox-ylamine, N-heptadecyl-N-octadecylhydroxylamine, N,N-dialkylhydroxylamine derived from hydrogenated tallow amine.

6. Nitrones, for example N-benzyl-alpha-phenylnitrone, N-ethyl-alpha-methylnitrone, N-octyl-alpha-heptylnitrone, N-lauryl-alpha-undecylnitrone, N-tetradecyl-alpha-tridecylnitrone, N-hexadecyl-alpha-pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-hepta-decylnitrone, N-octadecyl-alpha-hexadecylnitrone, nitrone derived from N,N-dialkylhydroxyl-amine derived from hydrogenated tallow amine.

7. Thiosynergists, for example dilauryl thiodipropionate or distearyl thiodipropionate.

8. Peroxide scavengers, for example esters of δ-thiodipropionic acid, for example the lauryl, stearyl, myristyl or tridecyl esters, mercaptobenzimidazole or the zinc salt of 2-mercapto-benzimidazole, zinc dibutyldithiocarbamate, dioctadecyl disulfide, pentaerythritol tetrakis(δ-dodecylmercapto)propionate.

9. Polyamide stabilisers, for example copper salts in combination with iodides and/or phosphorus compounds and salts of divalent manganese.

10. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

11. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1,3:2,4-bis(3',4'-dimethylbenzylidene)sorbitol, 1,3:2,4-di(paramethyldibenzylidene)sorbitol, and 1,3:2,4-di(benzylidene)sorbitol.

12. Fillers and reinforcing agents, for example calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example plasticisers, lubricants, levelling agents, emulsifiers, pigments, rheologic and thixotropic agents, flow-control agents, optical brighteners, flame-proofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)-phenyl]-5,7-di-tert-butylbenzofuran-2-one, 5,7-di-tert-butyl-3-[4-(2-stearoyloxyethoxy)phenyl]-benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzo-furan-2-one, 3-(3,4-dimethylphenyl)-5,7-di-tert-butylbenzofuran-2-one, 3-(2,3-di methylphel)-5,7-di-tert-butylbenzofuran-2-one.

In addition to the above-described base-polymerisable or crosslinkable binders, component (A), the composition may also include other binders as well. It is possible to use, for example, further olefinically unsaturated compounds. The unsaturated compounds may include one or more olefinic double bonds. They may be of low molecular mass (monomeric) or higher molecular mass (oligomeric). Examples of monomers having a double bond are alkyl acrylates or hydroxyalkyl acrylates or alkyl methacrylates or hydroxyalkyl methacrylates, such as methyl, ethyl, butyl, 2-ethylhexyl or 2-hydroxyethyl acrylate, isobornyl acrylate, methyl methacrylate or ethyl methacrylate. Silicone acrylates are also of interest. Further examples are acrylonitrile, acrylamide, methacrylamide, N-substituted (meth)acrylamides, vinyl esters such as vinyl acetate, vinyl ethers such as isobutyl vinyl ether, styrene, alkyl- and halostyrenes, N-vinylpyrrolidone, vinyl chloride or vinylidene chloride.

Examples of monomers having several double bonds are the diacrylates of ethylene glycol, propylene glycol, neopentyl glycol, hexamethylene glycol or bisphenol A, 4,4'-bis(2-acryloyl-oxyethoxy)diphenylpropane, trimethylolpropane triacrylate, pentaerythritol triacrylate or pentaerythritol tetraacrylate, vinyl acrylate, divinyl benzene, divinyl succinate, diallyl phthalate, triallyl phosphate, triallyl isocyanurate or tris(2-acryloylethyl)isocyanurate.

Examples of polyunsaturated compounds of high molecular mass (oligomers) are acrylated epoxy resins, acrylated polyesters or polyesters containing vinyl ether groups or epoxy groups, polyurethanes and polyethers. Further examples of unsaturated oligomers are unsaturated polyester resins which are mostly prepared from maleic acid, phthalic acid and one or more diols and have molecular weights of about 500 to 3000. In addition, it is also possible to employ vinyl ether monomers and oligomers, and also maleate-terminated oligomers with polyester, polyurethane, polyether, polyvinyl ether and epoxy main chains. In particular, combinations of vinyl ether-carrying oligomers and polymers as are described in WO 90/01512 are very suitable. Also suitable are copolymers of vinyl ether and maleic acid-functionalised monomers. Unsaturated oligomers of this kind can also be referred to as prepolymers.

Particularly suitable examples are esters of ethylenically unsaturated carboxylic acids and polyols or polyepoxides, and polymers having ethylenically unsaturated groups in the chain or in side groups, such as unsaturated polyesters, polyamides and polyurethanes and copolymers thereof, alkyd resins, polybutadiene and butadiene copolymers, polyisoprene and isoprene copolymers, polymers and copolymers having (meth)acrylic groups in side chains, and mixtures of one or more such polymers.

If, in addition, use is made of such radically curable monomers, oligomers/polymers then it is judicious to add a further photoinitiator or thermal radical initiator which dissociates into radicals. Such photoinitiators are known and are produced industrially. Examples are benzophenone, benzophenone derivatives, acetophenone, acetophenone derivatives, for example α-hydroxycycloalkyl phenyl ketones, dialkoxyacetophenones, α-hydroxy- or α-aminoacetophenones, 4-aroyl-1,3-dioxolanes, benzoin alkyl ethers and benzil ketals, monoacyl phosphine oxides, bisacylphosphine oxides, ferrocenium compounds or titanocenes.

Examples are specified in EP-A-284 561. Polymer systems of this kind in which curing/crosslinking takes place by different mechanisms are also referred to as hybrid systems.

It is also possible to add non-reactive binders to the novel compositions, which is particularly judicious if the anionically polymerisable or crosslinkable organic material, component (A) is a liquid or viscous substance. The amount of the non-reactive binder may be, for example, 5-95%, preferably 10-90% and, in particular, 40-90% by weight, based on the weight of component (A). The choice of non-reactive binder is made in accordance with the field of use and with the properties required for this use, such as the possibility for development in aqueous and organic solvent systems, adhesion to substrates, and sensitivity to oxygen.

Examples of suitable binders are polymers having a molecular weight of around 5000-2,000,000, preferably 10,000-1,000,000. Examples are homo- and copolymeric acrylates and methacrylates, for example copolymers of methyl methacrylate/ethyl acrylate/methacrylic acid, poly(alkyl methacrylates), poly(alkyl acrylates); cellulose esters and ethers, such as cellulose acetate, cellulose acetate butyrate, methylcellulose, ethylcellulose; polyvinylbutyral, polyvinylformal, cyclised rubber, polyethers such as polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers such as polycaprolactam and poly(hexamethylene adipamide) and polyesters such as poly(ethylene glycol terephtalate) and poly(hexamethylene glycol succinate).

The curable compositions according to the invention are prepared according to methods known in the art. The component (B), i.e. the thermolatent base represented by formula (I), and optional further additives may be added to component (A), i.e. an anionically polymerisable or crosslinkable organic material, and optional additional binders, individually or mixed with one another.

The incorporation of the component (B) and optional further additives into component (A) and optional binders is carried out by known methods such as dry mixing in the form of powder or wet mixing in the form of solutions or suspensions. Suitable solvents are, for example, dimethyl formamide, tetrahydrofurane, methyl ethyl ketone or ethyl acetate. Usual mixing apparatus are, for example, stirrers, kneaders, rollers, or in case of solid substances dry mixers.

The novel curable compositions may be employed for various purposes, preferably as coating compositions. The novel curable compositions are suitable, for example, as coating materials for substrates of all kinds, examples being wood, textiles, paper, ceramic, glass, plastics such as polyesters, polyethylene terephthalate, polyolefins or cellulose acetate, especially in the form of films, and also metals such as Al, Cu, Ni, Fe, Zn, Mg or Co and GaAs, Si or $SiO_2$.

The instant coating compositions are particularly suitable both for metal finish coatings and solid shade finishes of automobiles, especially in the case of retouching finishes, as well as various coil coating applications. The coating compositions in accordance with the invention are preferably applied in the conventional manner by two methods, either by the single-coat method or by the two-coat method. In the latter method, a pigment-containing base coat is applied first and then a covering coat of clear lacquer over it.

When water-soluble, water miscible or water dispersible coatings are desired ammonium salts of acid groups present in the resin are formed.

The thermolatent bases, component (B), are particularly useful when no organic solvent or water is present in the coating composition. This is typically the case for powder coatings.

Powder coating is a known technology and is described, for example, in "Ullmann's Encyclopedia of Industrial Chemistry, Fifth, Completely Revised Edition, Volume A 18", pages 438 to 444 (1991). In the powder coating process, a powder is generally fluidized with supply of air, electrostatically charged and applied to an earthed, preferably metallic substrate. The substrate is subsequently heated, in the course of which the adhering powder melts, coalesces and forms a coherent film on the metal surface. Since powder coating requires no solvent, this technology is especially friendly to the environment.

The manner in which the powder is brought into contact with the workpiece to be coated characterizes the various application techniques, for example electrostatic powder spraying with corona or triboelectric pistols, electrostatic fluidized-bed sintering or by using magnetic brush technology.

The novel curable compositions may also be employed as adhesives, including pressure sensitive adhesives, as laminating resins, for the coating or encapsulation of electrical or electronic components, or as coatings for optical fibres.

It is also possible to apply the curable composition of the invention as a liquid composition, a solution or suspension to the substrate. The choice of solvent and the concentration depend predominantly on the type of composition and the coating process. The solvent should be inert: in other words, it should not undergo any chemical reaction with the components and should be capable of being removed again after the coating operation, in the drying process. Examples of suitable solvents are ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate.

Using known coating processes, the solution is applied uniformly to a substrate, for example by spin coating, dip coating, knife coating, curtain coating, brushing, spraying, especially by electrostatic spraying and reverse roll coating, and by electrophoretic deposition.

The amount applied (layer thickness) and the nature of the substrate (layer support) are functions of the desired field of application. The range of layer thicknesses generally comprises values from about 0.1 µm to more than 100 µm.

Curing of the curable composition of the invention to form coatings or the like is carried out in a manner customarily employed in coating technology. Thermal curing means generally heating the composition at a temperature between 60° C. and 250° C., preferably between 80° C. and 150° C. In case of thermosetting powder coatings the preferred temperature range is between 120° C. and 200° C.

If photolatent bases are present in the composition, the composition may be cured by subjecting the composition to irradiation with a light having a wavelength of from 200 nm to 650 nm, preferably 250 nm to 400 nm.

In some cases it may be advantageous to carry out heating during or after exposure to light. In this way it is possible in many cases to accelerate the crosslinking reaction.

Curing time may be, for example, in the range of from 1 to 60 minute for thermosetting coatings.

This invention also relates to the use of a compound of formula (I)

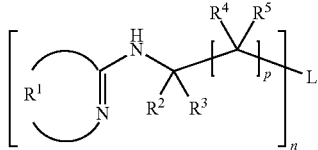

as a curing catalyst for thermally induced base-catalysed polymerisation or crosslinking reactions, in particular for curing compositions comprising component (A), wherein $R^1$, $R^2$, $R^3$, $R^4$, $R^5$, L, p and n have the meanings and preferred meanings stated above.

Further, the invention relates to the use of the compound of formula (I) for the preparation of coating compositions, especially powder coating compositions, or adhesive compositions.

In another aspect, this invention relates to polymerised or crosslinked novel compositions, for example coatings or bonded material produced by curing of a curable composition of the present invention, as described above.

In another aspect, this invention relates to a coating or a bonded article which coating or bonded article comprises a compound of formula (V)

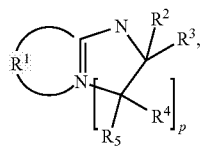

wherein the $R^1$, $R^2$, $R^3$, $R^4$, $R^5$ and p are as defined above, and a polymerised or crosslinked organic material.

Some of the compounds of formula (I) are known compounds. A number of compounds of formula (I) wherein L is a specific leaving group are novel compounds. The present invention further relates to a compound of formula (III),

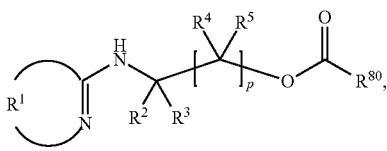

wherein, $R^1$ is a $C_2$-$C_{20}$ ring system, either a monocyclic ring system, which contains up to two heteroatoms of S or N or a polycyclic ring system, which contains one or more heteroatoms of S or N, said ring system is unsubstituted or substituted by $C_1$-$C_{18}$alkyl; $C_1$-$C_{18}$alkyl, which is substituted by E and/or interrupted by D; $C_5$-$C_{12}$cycloalkyl;

$C_5$-$C_{12}$cycloalkyl, which is substituted by E and/or interrupted by D; $C_2$-$C_{18}$alkenyl;

$C_2$-$C_{18}$alkinyl; $C_6$-$C_{16}$aryl; $C_6$-$C_{18}$aryl, which is substituted by G; $C_2$-$C_{18}$heteroaryl; $C_2$-$C_{18}$heteroaryl, which is substituted by G; $C_1$-$C_{18}$alkoxy; $C_1$-$C_{18}$alkoxy, which is substituted by E and/or interrupted by D; $C_1$-$C_{18}$alkylthio; $C_1$-$C_{18}$alkylthio, which is substituted by E and/or interrupted by D; $C_1$-$C_{18}$aralkyl; $C_1$-$C_{10}$aralkyl, which is substituted by G;

halogen; oxo; OH; SH; CN; $NH_2$; COOH; $NHR^6$; $NR^7R^8$; $CONH_2$; $CONR^9R^{10}$; $COR^{11}$; $C(O)OR^{12}$; $SO_2R^{13}$; $SO_3R^{14}$; $SO_2NHR^{15}$; $SO_2NR^{16}R^{17}$;

or said ring system is substituted by one or more groups of formula $$\text{(IV)}$$

$R^2$, $R^3$, $R^4$ and $R^5$ are independently of each other and each $R^4$ or $R^5$ independently from any other $R^4$ or $R^5$ are H; $C_1$-$C_{18}$alkyl; $C_1$-$C_{18}$alkyl, which is substituted by E and/or interrupted by D; $C_5$-$C_{12}$cycloalkyl; $C_5$-$C_{12}$cycloalkyl, which is substituted by E; $C_6$-$C_{12}$aryl; $C_6$-$C_{18}$aryl, which is substituted by G; $C_2$-$C_{18}$heteroaryl; $C_2$-$C_{18}$heteroaryl, which is substituted by G;

$C_1$-$C_{18}$alkoxy; $C_1$-$C_{18}$alkoxy, which is substituted by E and/or interrupted by D; $C_7$-$C_{18}$aralkyl;

$C_7$-$C_{18}$aralkyl, which is substituted by G; $NHR^{18}$, $NR^{19}R^{20}$, COOH;

or $R^2$ and $R^3$, $R^4$ and $R^5$, or $R^2$ and $R^4$ form an organic bridging group completing, together with the carbon atom, they are linked to, a carbocyclic or heterocyclic ring of 5 to 12 ring atoms in total;

or two of $R^5$, which are linked to adjacent carbon atoms, form an organic bridging group completing, together with the carbon atom, they are linked to, a carbocyclic or heterocyclic ring of 5 to 12 ring atoms in total;

D is —CO—; —COO—; —S—; —SO—; —$SO_2$—; —O—; —$NR^{21}$—; —$SiR^{22}R^{23}$—; —$POR^{24}$—; —$CR^{25}$=$CR^{26}$—; or —C≡C—; E is $OR^{27}$; $SR^{28}$; $SOR^{29}$; $SO_2R^{30}$; $NR^{31}R^{32}$; $COR^{33}$; $COOR^{34}$; $CONR^{35}R^{36}$; POR $(R^{37})_2$; $Si(R^{38})_3$; CN; Cl, Br, or I; and G is E or $C_1$-$C_{18}$alkyl;

$R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$ and $R^{38}$ are independently of each other $C_1$-$C_{18}$alkyl; $C_1$-$C_{18}$alkyl, which is interrupted by —O—; $C_6$-$C_{18}$aryl; $C_6$-$C_{18}$aryl, which is substituted by $C_1$-$C_{18}$alkyl or $C_1$-$C_{18}$alkoxy; $C_7$-$C_{18}$aralkyl; $C_7$-$C_{18}$aralkyl, which is substituted by G $C_2$-$C_{18}$heteroaryl;

or $R^7$ and $R^8$, $R^9$ and $R^{10}$, $R^{16}$ and $R^{17}$, $R^{19}$ and $R^{20}$, $R^{29}$ and $R^{30}$, or $R^{33}$ and $R^{34}$ form an organic bridging group completing, together with the nitrogen atom, they are linked to, a heterocyclic ring of 5 to 7 ring atoms in total;

$R^{80}$ is $C_1$-$C_{18}$alkoxy, $OC_6$-$C_{18}$aryl, $NHC_6$-$C_{18}$aryl, $NHC_1$-$C_{18}$alkyl; p is an integer of 1 or 2, with the proviso that, if p is 1 and the ring system is pyridine or pyrimidine, $R^3$ and $R^4$ is not phenyl, or, if p is 1 and the rig system is pyrimidine, said pyrimidine ring is not substituted by halogen.

Preferred compounds are compounds of formula (III), wherein $R^1$ is a mono- or polycyclic $C_2$-$C_{20}$ ring system, which contains up to 2 heteroatoms of S or N and/or is unsubstituted or substituted by $C_1$-$C_{18}$alkyl;

$R^2$, $R^3$, $R^4$ and $R^5$ are independently of each other and each $R^4$ or $R^5$ independently from any other $R^4$ or $R^5$ are H or $C_1$-$C_{18}$alkyl, $R^{80}$ is $C_1$-$C_{18}$alkoxy, $OC_6$-$C_{18}$aryl, $NHC_6$-$C_{18}$aryl, $NHC_1$-$C_{18}$alkyl; an p is an integer of 1 or 2.

More preferred are compounds of formulae (I-1) to (I-21) and (I-23), wherein L is OCONHMe, OCONHEt, OCONHPh, OCOOMe, OCOOtBu, OCOOPh, OCOOCH$_2$Ph.

The compounds of component (B) may be prepared by various known techniques. For example, one method of preparation consists of reacting a halo-substituted heterocycle with an appropriate amine, as described by D.-H. Yang et al., J. Chem. Res. 9, 2006, 600-601, V. Birman et al., Org. Lett. 9(1), 2007, 37-40 or M. J. Weiss, C. R. Hauser, J. Am. Chem. Soc. 72, 1950, 1858-1859. Another way of preparation is reacting an amino-substituted heterocycle with a suitable epoxide or an alkylating agent, as described by A. P. Gray et al., J. Am. Chem. Soc., 81, 1959, 4351-4355 or W. H. Yanko et al., J. Am. Chem. Soc. 67, 1945, 664-668 or F. C. Whitmore et al., J. Am. Chem. Soc. 67, 1945, 393.

The hydroxy or amino group of the component (B), corresponding to the leaving group L in formula (I), may be further modified to obtain a better nucleophilic group L.

The curable compositions of the present invention have excellent storage stability by using thermolatent amidine bases described above. So-called one-pot systems with base-polymerisable oligomers or monomers have an extremely long storage life without special precautions which offer an advantage in terms of reduced handling prior immediate use and lower amounts of waste due to better pot-life. The doctorability time, i.e. the period before the compositions cures, which is needed to handle the composition is increased.

Further, the curable compositions may be prepared by elevated temperature, for example by extrusion which is of particular interest for the production of powder coatings. Generally, powder coatings may be obtained at temperatures lower than the temperature which may activate the thermolatent base. Suitable temperature for manufacturing powder coatings may be of from 80 to 120° C. Thus, the temperature range of the preparation of the curable composition as well as of the application is increased.

The coatings obtained by curing the composition of the invention show less yellowing at the time after preparation as well as after a certain time. Moreover, the leveling of coatings, preferably those obtained by applying a powder coating of the invention, is improved.

The definitions and preferences given for the curable composition above apply in any combination as well as in any combination for the other aspects of the invention.

The following examples are for illustrative purposes only and are not to be construed to limit the instant invention in any manner whatsoever. Unless otherwise indicated, parts and percentages mentioned in the description or claims are by weight, and room temperature denotes a temperature of the range 20-25° C. Reactions are carried out under a nitrogen atmosphere and in the absence of light, unless otherwise stated.

Apparatus, etc. employed in measurement are as follows:
$^1$H NMR: Bruker 300 MHz spectrometer
IR spectroscopy: Nicolet 380 FT-IR spectrometer

EXAMPLES

Example 1

Reference Example

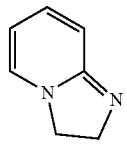

1

The compound is prepared according to V. Birman et al., J. Am. Chem. Soc. 126, 2004, 12226-12227.

Example 2

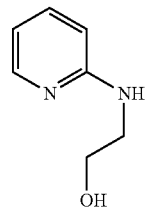

2

The compound is prepared according to V. Birman et al., J. Am. Chem. Soc. 126, 2004, 12226-12227.

Example 3

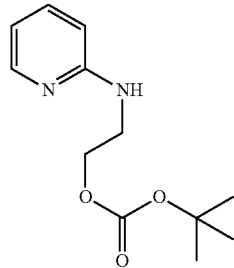

3

0.5 g of 4-dimethylamino-pyridine and 28 ml (0.2 mol) of triethylamine are added to a solution of 13.8 g (0.1 mol) of 2-(pyridine-2-ylamino)ethanol (2) in 50 ml of tetrahydrofurane. Then, a solution of 26.2 g (0.12 mol) of di-t-butyl-dicarbonate in 50 ml of tetrahydrofurane is added over 10 minutes, and the resulting mixture is stirred at room temperature for 20 hours. The solvent is evaporated, and the residue is chromatographed on silica gel with dichloromethane-ethyl acetate (9:1 to 5:1) to obtain 17.3 g of 3 as a light yellow oil.

$^1$H NMR (300 MHz, CDCl$_3$): 8.08 (d, 1H, J=5.1 Hz), 7.40 (m, 1H), 6.57 (m, 1H), 6.41 (d, 1H, J=8.4 Hz), 4.8 (bs, NH), 4.26 (t, 2H, J=5.4 Hz), 3.64 (m, 2H), 1.49 (s, t-Bu).

Example 4

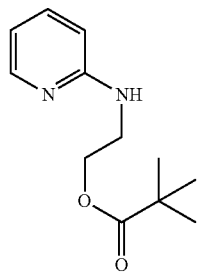

4

0.05 g of 4-dimethylamino-pyridine and 1.6 ml (0.011 mol) triethylamine are added to a solution of 1.38 g (0.01 mol) of 2-(pyridine-2-ylamino)-ethanol (2) in 10 ml of tetrahydrofurane. 1.32 g (0.011 mol) pivaloylchloride are then added over 10 minutes, and the resulting mixture is stirred at room temperature for 20 hours. The mixture is poured in 100 ml of ice water, and the precipitated oil is extracted 4× with 20 ml of dichloromethane. The combined extracts are washed with water and dried over $MgSO_4$. The solvent is then evaporated, and the residue is chromatographed on silica gel with dichloromethane-ethyl acetate (8:1 to 8:2) to obtain 1.39 g of 4 a light yellow oil.

$^1$H NMR (300 MHz, $CDCl_3$): 8.08 (d, 1H, J=5.1 Hz), 7.40 (m, 1H), 6.58 (m, 1H), 6.43 (d, 1H, J=8.4 Hz), 4.8 (bs, NH), 4.26 (t, 2H, J=5.4 Hz), 3.60 (m, 2H), 1.19 (s, t-Bu).

Example 5

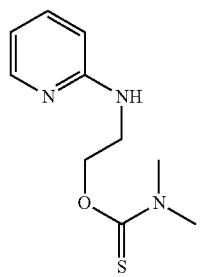

5

0.58 g (0.0132 mol) of sodium hydride (55% in mineral oil) are added to a solution of 1.66 g (0.012 mol) of 2-(pyridin-2-ylamino)-ethanol (2) in 6 ml of dimethylformamide, and the resulting mixture is stirred for 30 minutes. The mixture is then cooled to 3° C., and 1.65 g (0.0132 mol) of dimethylthiocarbamoyl chloride are added over 10 minutes. The resulting mixture is stirred for 2 hours and then poured in 20 ml of ice water. The precipitated oil is extracted 3× with 25 ml of dichloromethane, and the combined extracts are washed with water and dried over $MgSO_4$. The solvent is then evaporated, and the residue is chromatographed on silica gel with dichloromethane-ethyl acetate (7:3) to obtain 1.95 g of 5 as a yellow oil.

$^1$H NMR (300 MHz, $CDCl_3$): 8.08 (d, 1H, J=5.1 Hz), 7.41 (m, 1H), 6.58 (m, 1H), 6.43 (d, 1H, J=8.4 Hz), 4.8 (bs, NH), 4.70 (t, 2H, J=5.4 Hz), 3.70 (m, 2H), 3.36 (s, $CH_3$), 3.08 (s, $CH_3$).

Example 6

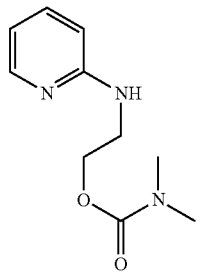

6

0.58 g (0.0132 mol) of sodium hydride (55% in mineral oil) are added to a solution 1.66 g (0. 012 mol) of 2-(pyridine-2-ylamino)-ethanol (2) in 6 ml of dimethylformamide, and the resulting mixture is stirred for 30 minutes. The mixture is then cooled to 3° C., and 1.42 g (0.0132 mol) of dimethylcarbamoyl chloride are added over 10 minutes. The resulting mixture is stirred for 2 hours and then poured in 100 ml of ice water. The precipitated solid is extracted 5×20 ml of dichloromethane, and the combined extracts are washed with water and dried over $MgSO_4$. The solvent is evaporated, and the residue is chromatographed on silica gel with dichloromethane-ethyl acetate (3:7). The pure fractions are recrystallized from hexane-ethyl acetate to obtain 1.65 g of 6 as a white solid (mp. 49-52° C.).

$^1$H NMR (300 MHz, $CDCl_3$): 8.08 (d, 1H, J=4.8 Hz), 7.40 (m, 1H), 6.58 (m, 1H), 6.43 (d, 1H, J=8.4 Hz), 4.8 (bs, NH), 4.29 (t, 2H, J=5.4 Hz), 3.58 (m, 2H), 2.91 (s, $CH_3$), 2.88 (s, $CH_3$).

Example 7

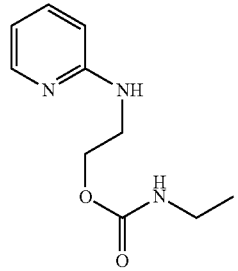

7

160 mg of 4-dimethylaminopyridine and 5.05 ml (0.064 mol) of ethyl isocyanate are added to a solution of 7.6 g (0.055 mol) of 2-(pyridine-2-ylamino)ethanol (2) in 35 ml of dichloromethane, and the resulting mixture is stirred at room temperature for 20 hours. The solvent is evaporated, and the residue is chromatographed on silica gel with dichloromethane-ethyl acetate (1:1 to 3:7). The pure fractions are recrystallized from dichloromethane-hexane to obtain 12.9 g of 7 as a white solid (mp. 80-83° C.).

$^1$H NMR (300 MHz, CDCl$_3$): 8.07 (d, 1H, J=5.1 Hz), 7.39 (m, 1H), 6.55 (m, 1H), 6.41 (d, 1H, J=8.4 Hz), 5.04 (bs, 2NH), 4.26 (m, 2H), 3.55 (m, 2H), 3.20 (m, 2H), 1.12 (m, 3H).

Example 8

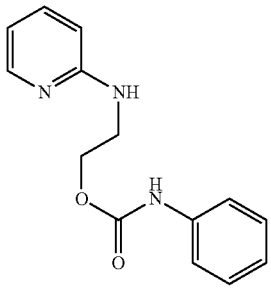

8

60 mg of 4-dimethylaminopyridine and 1.31 g (0.011 mol) of phenyl isocyanate are added to a solution of 1.38 g (0.01 mol) of 2-(pyridine-2-ylamino)ethanol (2) in 10 ml of dichloromethane, and the resulting mixture is stirred at room temperature for 75 hours. The solvent is evaporated, and the residue is chromatographed on silica gel with dichloromethane-ethyl acetate (3:7). The pure fractions are recrystallized from dichloromethane-hexane to obtain 1.84 g of 8 as a white solid (mp. 80-81° C.).

$^1$H NMR (300 MHz, CDCl$_3$): 8.09 (d, 1H, J=4.2 Hz), 7.46-7.26 (m, C$_6$H$_5$), 7.09 (m, 1H), 6.75 (bs, NH), 6.60 (m, 1H), 6.45 (d, 1H, J=8.4 Hz), 4.90 (bs, NH), 4.38 (t, 2H, J=5.4 Hz), 3.66 (m, 2H).

Example 9

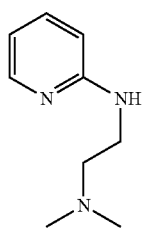

9

The compound is prepared as described by K. Kovacs, T. Vajda, Chemistry & Industry, 1959, 259.

Example 10

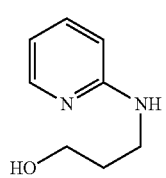 [SMILES: OCCCNc1ccccn1]

10

The compound is prepared as described by D. Heckmann et al., Angew. Chem., Internat. Ed. 46(19), 2007, 3571-3574.

Example 11

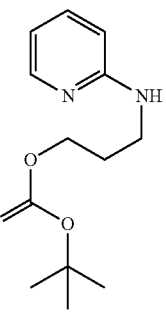

11

A solution of 2.62 g (0.012 mol) of di-tert-butyl-dicarbonate in 4 ml of tetrahydrofurane is added to a solution of 1.52 g (0.01 mol) of 3-(pyridine-2-ylamino)-propane-1-ol (10), 0.055 g of 4-dimethylamino-pyridine and 2.8 ml (0.02 mol) of triethylamine in 2 ml of tetrahydrofurane, and the resulting mixture is stirred at room temperature for 24 hours. The solvent is then evaporated, and the residue is chromatographed on silica gel with dichloromethane-ethyl acetate (9:1) to obtain 1.02 g 11 as a colorless solid which solidifies on standing (mp. 55-57° C.).

$^1$H NMR (300 MHz, CDCl$_3$): 8.07 (d, 1H, J=4.2 Hz), 7.41 (m, 1H), 6.56 (m, 1H), 6.39 (d, 1H, J=8.4 Hz), 4.7 (bs, NH), 4.19 (t, 2H, J=5.7 Hz), 3.41 (m, 2H), 1.98 (m, 2H), 1.49 (s, t-Bu).

Example 12

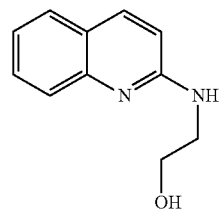 [SMILES: OCCNc1ccc2ccccc2n1]

12

A mixture of 16.3 g (0.1 mol) of 2-chloroquinoline and 24.5 g (0.4 mol) of 2-aminoethanol is heated to 170° C. for 21 hours. The mixture is then cooled to room temperature, and 180 ml of ice water is added thereto. The precipitated solid is dissolved in 120 ml of dichloromethane, the resulting solution is washed 2× with 15 ml of water, dried over MgSO$_4$ and evaporated. The residue is recrystallized from dichloromethane-ethyl acetate to obtain 13.04 g of 12 as a light yellow solid (mp. 119-122° C.).

$^1$H NMR (300 MHz, CDCl$_3$): 7.79-7.49 (m, 4H), 7.26-7.19 (m, 1H), 6.63 (d, 1H, J=9 Hz), 6.0 (bs, NH), 5.34 (bs, NH), 3.86 (m, 2H), 3.66 (m, 2H).

Example 13

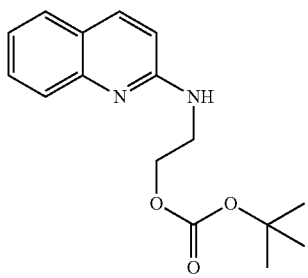

13

A solution of 2.62 g (0.012 mol) of di-t-butyl-dicarbonate in 5 ml of tetrahydrofurane is added to a solution of 1.88 g (0.01 mol) of 2-(quinoline-2-ylamino)-ethanol (12), 0.055 g of 4-dimethylamino-pyridine and 2.8 ml (0.02 mol) of tri-ethylamine in 7 ml of tetrahydrofurane, and the resulting mixture is stirred at 40° C. for 1 hour. The solvent is then evaporated, and the residue is chromatographed on silica gel with dichloromethane-ethyl acetate (9:1). The pure fractions are recrystallized from hexane-ethyl acetate to obtain 1.37 g of 13 as a colorless solid (mp. 113-116° C.).

$^1$H NMR (300 MHz, CDCl$_3$): 7.83-7.50 (m, 4H), 7.26-7.19 (m, 1H), 6.56 (m, 1H), 6.63 (d, 1H, J=8.7 Hz), 5.1 (bs, NH), 4.34 (t, 2H, J=5.7 Hz), 3.86 (m, 2H), 1.49 (s, t-Bu).

Example 14

Reference Example

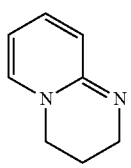

14

The compound is prepared as described by T. Yamazaki et al., Yakugaku Zasshi, 88(2), 1968, 212-215.

Example 15

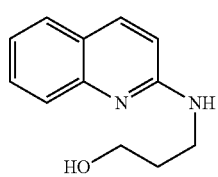

15

The compound is prepared as described by M. Nagata et al., Yakugaku Zasshi, 83, 1963, 682-689.

Example 16

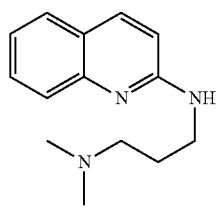

16

A mixture of 8.15 g (0.05 mol) of 2-chloroquinoline and 15.3 g (0.15 mol) of 3-dimethylaminopropylamine is heated at 170° C. for 17 hours. The resulting mixture is then cooled to room temperature, and 80 ml of ice water is added thereto. The precipitated oil is extracted with 10 ml of dichloromethane, the resulting solution is washed with 40 ml of water and 25 ml of 2M Na$_2$CO$_3$, the separated organic phase is dried over MgSO$_4$ and evaporated to obtain 9.5 g 16 as a light yellow oil.

$^1$H NMR (300 MHz, CDCl$_3$): 7.80-7.40 (m, 4H), 7.20-7.10 (m, 1H), 6.61 (d, 1H, J=9 Hz), 5.65 (bs, NH), 3.56 (m, 2H), 2.42 (t, 2H, J=6.6 Hz), 2.25 (s, 2×CH$_3$); 1.81 (m, 2H).

Example 17

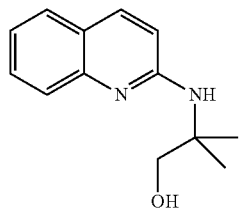

17

A mixture of 16.3 g (0.1 mol) of 2-chloroquinoline and 26.8 g (0.3 mol) of 2-amino-2-methylpropanol is heated at 170° C. for 48 hours. The resulting mixture is then cooled to room temperature, and 270 ml of ice water is added thereto. The product is filtered off and dried to obtain 16.15 g of a solid which is recrystallized twice from ethanol to obtain 7.9 g of 17 as a gray solid.

$^1$H NMR (300 MHz, CDCl$_3$): 7.8-6.6 (m, 6H), 5.0 (bs, NH), 3.71 (s, 2H), 1.43 (s, 6H).

Example 18

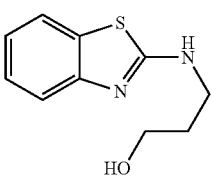

18

The compound is prepared as desribed by V. Birman et al., Org. Lett. 9(1), 2007, 37-40.

Example 19

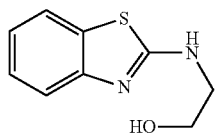

The compound is prepared as desribed by M. Kobayashi et al., Tetrahedron Lett., 47(26), 2006, 4347-4350.

Example 20

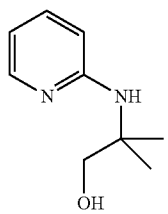

A mixture of 16.6 g (0.105 mol) of 2-bromopyridine and 29 g (0.325 mol) of 2-amino-2-methylpropano (29 g, 0.325 mol) is heated at 170° C. for 84 hours. The resulting mixture is then cooled to room temperature, and 200 ml of ice water is added thereto. The product is extracted 4× with 30 ml of dichloromethane, the combined extracts are dried over MgSO$_4$ and evaporated to obtain 12.7 g of a brown oil which is chromatographed on silica gel with ethyl acetate-hexane (1:1) to obtain 7.15 g of 20 as a light yellow solid (m.p. 90-94° C.).

$^1$H NMR (300 MHz, CDCl$_3$): 7.97 (d, 1H, J=7.8 Hz), 7.45-7.35 (m, 1H), 6.58-6.53 (m, 1H), 6.42 (d, 1H, J=8.4 Hz), 4.5 (bs, NH), 3.62 (s, 2H), 1.34 (s, 6H).

Example 21

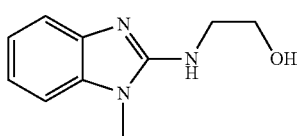

The compound is prepared as desribed by A. M. Simonov et al., Khimiya Geterotsiklicheskikh Soedinenii, 6, 1975, 826-828.

Example 22

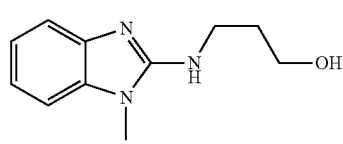

The compound is prepared as desribed by V. A. Anisimova et al., Pharm. Chem. J. 36(9), 2002, 468-473.

Example 23

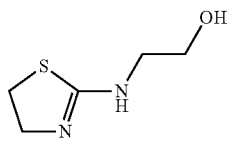

The compound is prepared as desribed by R. C. Clapp et al., J. Org. Chem., 28(8), 1964, 2172-2174.

Example 24

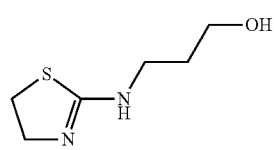

The compound is prepared as desribed by R. C. Clapp et al., J. Heterocycl. Chem., 7(6), 1970, 1357-1361.

Example 25

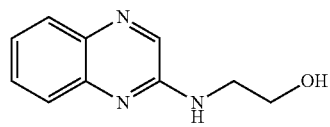

The compound is prepared as desribed by H. Otomasu et al., Yakugaku Zasshi, 90(11), 1970, 1391-1395.

Example 26

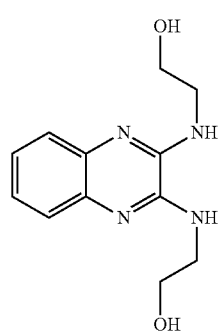

The compound is prepared as desribed by I. N. Goncharov et al., Zhurnal Obshchei Khimii 32, 1962, 3332-3339.

Example 27

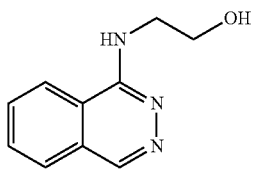

The compound is prepared as desribed by R. N. Castle et al., J. Heterocycl. Chem., 3(3), 1966, 381-383.

Example 28

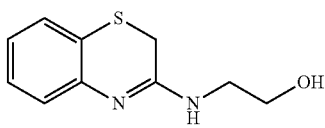

The compound is prepared as desribed by K. Bhandari et al., Indian. J. Chem., Sect. B, 17B(2), 1979, 107-110.

Example 29

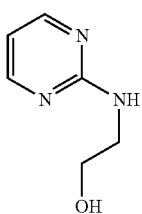

The compound is prepared as desribed by J. N. Singh et al., J. Indian Chem. Soc., 40, 1963, 195-198.

Example 30

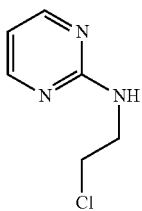

The compound is prepared as desribed by J. N. Singh et al., J. Indian Chem. Soc. 43(5), 1966, 308-310.

Example 31

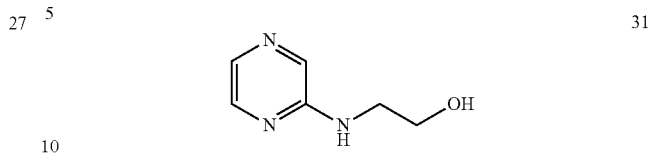

The compound is prepared as desribed by G. Cignarella et al., J. Med. Chem. 8(3), 1965, 326-331.

Application Examples

A powder coating formulation consisting of an acidic functional polyester and an epoxy functional polymer that cures without a catalyst at 200° C. for 20 minutes is used. The solid coating formulation is dissolved at 50% solids in methyl-isobutyl ketone for ease of application. The curing catalyst is added in varying amounts from 0.5 up to 1.5% by weight, based on solids. The thermolatent compounds are compared with imidazole or compound 1 as a reference base. The formulation is applied at wet thickness 250 μm using a wire bar. The solvent is evaporated at room temperature during 30 minutes, and the coating formulation is cured for given times and at the specified temperature (cf. Tables 2 to 4). The curing progress is evaluated using attenuated total reflection infrared (IR) spectroscopy. The fading of the epoxy-attributable peak at 899-921 cm$^{-1}$ in comparison to the stable reference peak at 814-841 cm$^{-1}$ is used for the calculation of the conversion of epoxy groups.

TABLE 2

Comparison of curing with imidazole and compound 1

| Reference base/ activated base | Amount [wt. %] | Conversion at 5' 100° C. [%] | Conversion at 15' 120° C. [%] |
| --- | --- | --- | --- |
| — | 0 | 0 | 13 |
| imidazole | 0.5 | 26 | 100 |
| 1 | 0.5 | 13 | 98 |

The color deviation or yellowing, resp., in ΔE is determined according to the CIELAB system. It is found that at a conversion after 15 min at 120° C. ΔE of the composition comprising 1 is 30% better than the corresponding value of the composition comprising imidazole.

TABLE 3

Comparison of imidazole with thermolatent bases (compounds 2, 3 and 7) at different concentrations, times and temperatures

| Reference base/ thermolatent base | Amount [wt. %] | Conversion at 5' 130° C. [%] | Conversion at 5' 150° C. [%] |
| --- | --- | --- | --- |
| Imidazole | 0.5 | 35 | 100 |
| 2 | 0.5 | 26 | 97 |
| 3 | 1.0 | 22 | 94 |
| 3 | 1.5 | 23 | 100 |
| 7 | 1.0 | 14 | 95 |
| 7 | 1.5 | 29 | 93 |

TABLE 4

Comparison of imidazole with thermolatent base (compound 16) at different temperatures

| Reference base/ thermolatent base | Amount [wt. %] | Conversion 5' 100° C. [%] | Conversion 5' 130° C. [%] | Conversion 5' 150° C. [%] | Conversion 5' 180° C. [%] |
|---|---|---|---|---|---|
| Imidazole | 1 | 53 | 74 | 100 | 100 |
| 16 | 1 | 0 | 0 | 20 | 100 |

The invention claimed is:

1. A curable composition comprising
(A) an organic material which is polymerisable or crosslinkable with a basic or nucleophilic catalyst,
(B) a compound of the formula

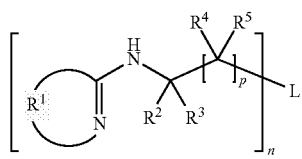

(I)

wherein
$R^1$ forms together with the carbon and nitrogen atom, it is linked to, a mono- or polycyclic $C_2$-$C_{20}$ ring system selected from the group consisting of imidazole, benzimidazole, thiazole, benzothiazole, pyrazole, oxazole, benzoxazole, isoxazole, isothiazole, 1,2,3-triazole, 1,2,4-triazole, tetrazole, 1,2,4-oxadiazole, 1,2,4-thiadiazole, 1,3,4-oxadiazole, 1,3,4-thiadiazole, pyridine, quinoline, isoquinoline, phenanthridine, pyridazine, pyrimidine, pyrazine, cinnoline, phthalazine, chinazoline, chinoxaline, chinazolinone, 1,3,5-triazine, 1,2,4,5-tetrazine, purine, xanthine, hypoxanthine, guanine, adenine, pteridine, pterine, 1,10-phenanthroline, 2,2'-bipyridine, 4,4'-bipyridine,

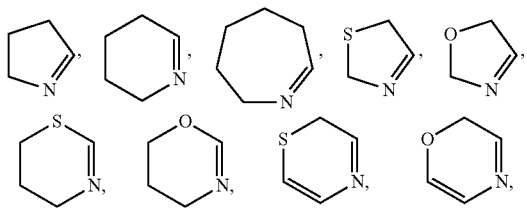

said ring system is unsubstituted or substituted by $C_1$-$C_8$alkyl; $C_5$-$C_7$cycloalkyl; $C_6$-$C_{12}$aryl; $C_6$-$C_{18}$aryl, which is substituted by G; $C_2$-$C_{18}$heteroaryl; $C_2$-$C_{18}$heteroaryl, which is substituted by G; $C_1$-$C_8$alkoxy; $C_1$-$C_8$alkoxy, which is substituted by E and/or interrupted by D; $C_7$-$C_{11}$aralkyl; $C_7$-$C_{11}$aralkyl, which is substituted by G;
halogen, OH, oxo, CN, $NH_2$, $NHR^6$, $NR^7R^8$, $CONH_2$, $CONR^9R^{10}$, $COR^{11}$, $C(O)OR^{12}$,
wherein $R^6$, $R^7$, $R^8$, $R^9$, $R^{10}$, $R^{11}$ and $R^{12}$ are independently of each other $C_1$-$C_8$alkyl; $C_1$-$C_8$alkyl, which is interrupted by —O—; $C_6$-$C_{12}$aryl; $C_6$-$C_{12}$aryl, which is substituted by $C_1$-$C_8$alkyl or $C_1$-$C_8$alkoxy; $C_7$-$C_{11}$aralkyl; $C_7$-$C_{11}$aralkyl, which is substituted by G;

or $R^7$ and $R^8$ form an organic bridging group completing, together with the nitrogen atom, they are linked to, a heterocyclic ring of 5 to 7 ring atoms in total;
or said ring system is further anellated by one or more benzene rings
$R^2$, $R^3$, $R^4$ and $R^5$ are independently of each other H; $C_1$-$C_{18}$alkyl; $C_1$-$C_{18}$alkyl, which is substituted by E and/or interrupted by D; $C_5$-$C_{12}$cycloalkyl; $C_5$-$C_{12}$cycloalkyl, which is substituted by E; $C_6$-$C_{12}$aryl; $C_6$-$C_{18}$aryl, which is substituted by G; $C_2$-$C_{18}$heteroaryl; $C_2$-$C_{18}$heteroaryl, which is substituted by G; $C_1$-$C_{18}$alkoxy; $C_1$-$C_{18}$alkoxy, which is substituted by E and/or interrupted by D; $C_7$-$C_{18}$aralkyl; $C_7$-$C_{18}$aralkyl, which is substituted by G; $NHR^{18}$, $NR^{19}R^{20}$, COOH;
or $R^2$ and $R^3$, $R^4$ and $R^5$, or $R^2$ and $R^4$ form an organic bridging group completing, together with the carbon atom, they are linked to, a carbocyclic or heterocyclic ring of 5 to 12 ring atoms in total;
or two of $R^5$, which are linked to adjacent carbon atoms, form an organic bridging group completing, together with the carbon atom, they are linked to, a carbocyclic or heterocyclic ring of 5 to 12 ring atoms in total;
D is —CO—; —COO—; —S—; —SO—; —$SO_2$—; —O—; —$NR^{21}$—; —$SiR^{22}R^{23}$—; —$POR^{24}$—; —$CR^{25}$=$CR^{26}$—; or —C≡C—;
E is $OR^{27}$; $SR^{28}$; $SOR^{29}$; $SO_2R^{30}$; $NR^{31}R^{32}$; $COR^{33}$; $COOR^{34}$; $CONR^{35}R^{36}$; $PO(R^{37})_2$; CN; or halogen; and
G is E or $C_1$-$C_{18}$alkyl;
$R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$ and $R^{37}$ are independently of each other $C_1$-$C_{18}$alkyl; $C_1$-$C_{18}$alkyl, which is interrupted by —O—; $C_6$-$C_{18}$aryl; $C_6$-$C_{18}$aryl, which is substituted by $C_1$-$C_{18}$alkyl or $C_1$-$C_{18}$alkoxy; $C_7$-$C_{18}$aralkyl; $C_7$-$C_{18}$aralkyl, which is substituted by G; $C_2$-$C_{18}$heteroaryl;
or $R^{19}$ and $R^{20}$, $R^{31}$ and $R^{32}$, or $R^{35}$ and $R^{36}$ form an organic bridging group completing, together with the nitrogen atom, they are linked to, a heterocyclic ring of 5 to 7 ring atoms in total;
L is a n-valent leaving group,
n is an integer of 1, 2, 3 or 4;
p is an integer of 1, 2, 3 or 4,
(C) a curing catalyst other than component (B) and
(D) at least one additive
if n is 1, L is halogen, OH, $OR^{40}$, $SR^{40}$, $OCOR^{40}$, $OCOOR^{41}$, $OCONR^{42}R^{43}$, $OCSNR^{42}R^{43}$, $OSO_2R^{40}$, $OSO_3R^{40}$, $NR^{42}R^{43}$, $S^+R^{42}R^{43}X^-$, $N^+R^{42}R^{43}R^{44}X^-$, $P^+R^{42}R^{43}X^-$, $NHCOR^{40}$, $OPO(OR^{40})_2$, $OPO(R^{46})(OR^{47})$, $OSi(R^{40})_3$;
wherein
$R^{40}$, $R^{42}$, $R^{43}$, $R^{44}$, $R^{45}$, $R^{46}$ and $R^{47}$ are independently of each other H, $C_1$-$C_{18}$alkyl or $C_1$-$C_{18}$alkyl, which is substituted by E and/or interrupted by D; $C_5$-$C_{12}$cycloalkyl, $C_5$-$C_{12}$cycloalkyl, which is substituted by E and/or interrupted by D; $C_6$-$C_{18}$aryl; $C_6$-$C_{18}$aryl, which is substituted by G; $C_7$-$C_{18}$aralkyl; $C_7$-$C_{18}$aralkyl, which is substituted by G; $C_2$-$C_{18}$heteroaryl; $C_2$-$C_{18}$heteroaryl, which is substituted by G;
or $R^{42}$ and $R^{43}$ form an organic bridging group completing, together with the nitrogen atom, they are linked to, a heterocyclic ring of 5 to 7 ring atoms in total;
or two of $R^{45}$ form a bridging group completing, together with the —OC—N—CO-group, they are linked to, a heterocyclic ring of 5 to 7 ring atoms in total;
$R^{41}$ is $C_1$-$C_{18}$alkyl or $C_1$-$C_{18}$alkyl, which is substituted by E and/or interrupted by D; $C_5$-$C_{12}$cycloalkyl, $C_5$-$C_{12}$cycloalkyl, which is substituted by E and/or interrupted by D; $C_6$-$C_{18}$aryl; $C_1$-$C_{18}$aryl, which is substituted by G; $C_2$-$C_{18}$heteroaryl; $C_2$-$C_{18}$heteroaryl, which is substituted by G;

$X^-$ is halide, hydroxide, $C_1$-$C_{18}$alkylsulfonate, $C_6$-$C_{18}$arylsulfonate, $R^{48}COO^-$, $HSO_4^-$ or $\frac{1}{2} SO_4^{2-}$, wherein $R^{48}$ is H, $C_1$-$C_{18}$alkyl or $C_1$-$C_{18}$alkyl, which is substituted by E and/or interrupted by D; $C_5$-$C_{12}$cycloalkyl, $C_5$-$C_{12}$cycloalkyl, which is substituted by E and/or interrupted by D; $C_6$-$C_{18}$aryl; $C_6$-$C_{18}$aryl, which is substituted by G; $C_2$-$C_{18}$heteroaryl; $C_2$-$C_{18}$heteroaryl, which is substituted by G;

if n is 2, L is —OCO—O—,

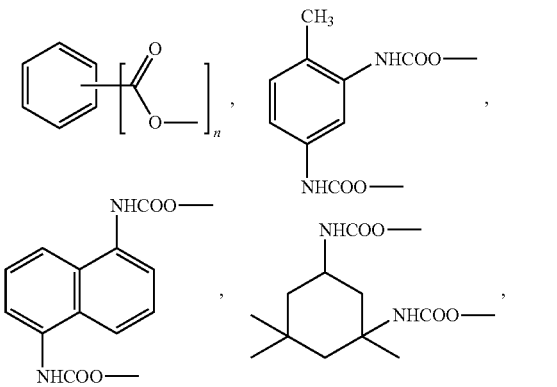

—OSO$_2$O—, —OCO—(CH$_2$)$_q$—COO—, —OSi(CH$_3$)$_2$O—, —OCON(CH$_2$)$_q$, wherein q is 0 or an integer of 1 to 10; or if n is 3 or 4, L is

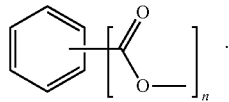

2. A composition according to claim 1, wherein $R^2$, $R^3$, $R^4$ and $R^5$ are independently of each other H; $C_1$-$C_8$alkyl; $C_5$-$C_8$cycloalkyl; $C_6$-$C_{18}$aryl; $C_6$-$C_{18}$aryl, which is substituted by G; $C_2$-$C_{18}$heteroaryl; $C_2$-$C_{18}$heteroaryl, which is substituted by G; $C_1$-$C_4$alkoxy; $C_7$-$C_{10}$aralkyl; NHR$^6$, NR$^7$R$^8$, wherein $R^6$, $R^7$ and $R^8$ are independently of each other $C_1$-$C_4$alkyl; $C_6$-$C_{12}$aryl; $C_6$-$C_{12}$aryl, which is substituted by $C_1$-$C_4$alkyl or $C_1$-$C_4$alkoxy; $C_7$-$C_{10}$aralkyl;

or $R^7$ and $R^8$ form an organic bridging group completing, together with the nitrogen atom, they are linked to, a heterocyclic ring of 5 to 7 ring atoms in total;

or $R^2$ and $R^3$, $R^4$ and $R^5$, or $R^2$ and $R^4$ form an organic bridging group completing, together with the carbon atom, they are linked to, a carbocyclic or heterocyclic ring of 5 to 7 ring atoms in total;

or two of $R^5$, which are linked to adjacent carbon atoms, form an organic bridging group completing, together with the carbon atom, they are linked to, a carbocyclic or heterocyclic ring of 5 to 7 ring atoms in total.

3. A composition according to claim 1, wherein $R^2$, $R^3$, $R^4$ and $R^5$ are independently of each other H or $C_1$-$C_4$alkyl, and p is an integer of 1 or 2.

4. A composition according to claim 1, wherein $R^1$ forms together with the carbon and nitrogen atom, it is linked to, a mono- or polycyclic $C_1$-$C_{20}$ ring system selected from the group consisting of imidazole, benzimidazole, thiazole, benzothiazole, oxazole, benzoxazole, isothiazole, pyridine, chinoline, isochinoline, phenanthridine, pyridazine, pyrimidine, pyrazine, cinnoline, phthalazine, chinazoline, chinoxaline, 1,3,5-triazine, purine, 1,10-phenanthroline, 2,2'-bipyridine and 4,4'-bipyridine;

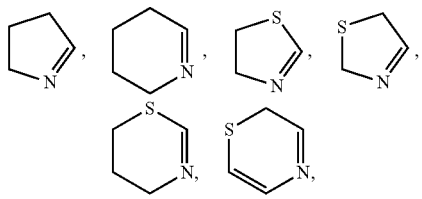

said ring system is unsubstituted or substituted by $C_1$-$C_4$alkyl; phenyl; phenyl, which is substituted by $C_1$-$C_4$alkyl, $C_1$-$C_4$alkoxy or halogen; $C_1$-$C_4$alkoxy; benzyl; phenethyl;

halogen, OH, NH$_2$, NHR$^6$, NR$^7$R$^8$, CONH$_2$, CONR$^9$R$^{10}$, COR$^{11}$, C(O)OR$^{12}$, wherein $R^6$, $R^7$, $R^8$, $R^9$, $R^{10}$, $R^{11}$ and $R^{12}$ are independently of each other $C_1$-$C_4$alkyl; phenyl; benzyl; phenethyl;

or $R^7$ and $R^8$ form an organic bridging group completing, together with the nitrogen atom, they are linked to, a heterocyclic ring of 5 to 6 ring atoms in total;

or said ring system is further anellated by one or more benzene rings.

5. A composition according to claim 1, wherein n is 1 and L is halogen, OH, OR$^{40}$, SR$^{40}$, OCOR$^{40}$, OCOOR$^{41}$, OCONR$^{42}$R$^{43}$, OCSNR$^{42}$R$^{43}$, NR$^{42}$R$^{43}$, wherein $R^{40}$, $R^{42}$, $R^{43}$ are independently of each other H, $C_1$-$C_8$alkyl; phenyl; or benzyl.

6. A composition according to claim 1, wherein component (A) is one of the following systems:

a) an acrylate copolymer having alkoxysilane or alkoxysiloxane side groups, b) a two-component system comprising a hydroxyl group-containing polyacrylate and/or polyester and an aliphatic or aromatic polyisocyanate, c) a two-component system comprising a functional polyacrylate and/or polyester and a polyepoxide, where the polyacrylate and/or polyester contains carboxyl or anhydride groups, d) a two-component system comprising a fluorine-modified or silicone-modified hydroxyl group-containing polyacrylate or polyester and an aliphatic or aromatic polyisocyanate, e) a two-component system comprising a (poly)ketimine and an aliphatic or aromatic polyisocyanate, f) a two-component system comprising a (poly)ketimine and an unsaturated acrylate resin or an acetoacetate resin or methyl α-acrylamidomethylglycolate, h) a two-component system comprising a (poly)oxazolidine and a polyacrylate containing anhydride groups, or an unsaturated acrylate resin or a polyisocyanate, i) a two-component system comprising an epoxy group-containing polyacrylate and a carboxyl group-containing polyacrylate, or a dicarboxylic acid, l) a polymer based on allyl glycidyl ether, m) a two-component system comprising a (poly)alcohol and a (poly)isocyanate,
n) a two-component system comprising an α,β-ethylenically unsaturated carbonyl compound and a compound which contains activated CH$_2$ groups.

7. A composition according to claim 1, wherein component (A) is an epoxy resin or a mixture of different epoxy resins.

8. A composition according to claim 1, wherein component (B) is present in an amount of from 0.01 to 15% by weight.

9. A composition according to claim 1, wherein the curable composition is a powder coating composition, or an adhesive composition.

10. A coating or a bonded article produced by curing of a curable composition according to claim 1.

11. A method of using a compound of formula (I) as a curing catalyst comprising
activating the catalyst and catalyzing a thermally induced base-catalysed polymerisation or crosslinking reaction, wherein formula (I) is shown below:

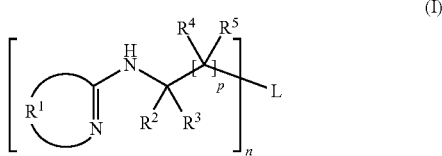

wherein
R$^1$ forms together with the carbon and nitrogen atom, it is linked to, a mono- or polycyclic C$_2$-C$_{20}$ ring system selected from the group consisting of imidazole, benzimidazole, thiazole, benzothiazole, pyrazole, oxazole, benzoxazole, isoxazole, isothiazole, 1,2,3-triazole, 1,2,4-triazole, tetrazole, 1,2,4-oxadiazole, 1,2,4-thiadiazole, 1,3,4-oxadiazole, 1,3,4-thiadiazole, pyridine, quinoline, isoquinoline, phenanthridine, pyridazine, pyrimidine, pyrazine, cinnoline, phthalazine, chinazoline, chinoxaline, chinazolinone, 1,3,5-triazine, 1,2,4,5-tetrazine, purine, xanthine, hypoxanthine, guanine, adenine, pteridine, pterine, 1,10-phenanthroline, 2,2'-bipyridine, 4,4'-bipyridine,

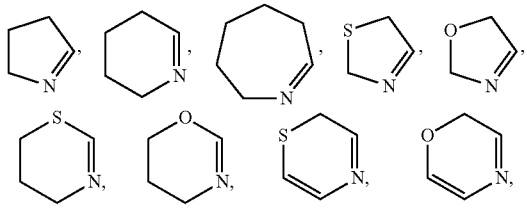

said ring system is unsubstituted or substituted by C$_1$-C$_8$alkyl; C$_5$-C$_7$cycloalkyl; C$_6$-C$_{12}$aryl; C$_6$-C$_{18}$aryl, which is substituted by G; C$_2$-C$_{18}$heteroaryl; C$_2$-C$_{18}$heteroaryl, which is substituted by G; C$_1$-C$_8$alkoxy; C$_1$-C$_8$alkoxy, which is substituted by E and/or interrupted by D; C$_7$-C$_{11}$aralkyl; C$_7$-C$_{11}$aralkyl, which is substituted by G; halogen, OH, oxo, CN, NH$_2$, NHR$^6$, NR$^7$R$^8$, CONH$_2$, CONR$^9$R$^{10}$, COR$^{11}$, C(O)OR$^{12}$,
wherein R$^6$, R$^7$, R$^8$, R$^9$, R$^{10}$, R$^{11}$ and R$^{12}$ are independently of each other C$_1$-C$_8$alkyl; C$_1$-C$_8$alkyl, which is interrupted by —O—; C$_6$-C$_{12}$aryl; C$_6$-C$_{12}$aryl, which is substituted by C$_1$-C$_8$alkyl or C$_1$-C$_8$alkoxy; C$_7$-C$_{11}$aralkyl; C$_7$-C$_{11}$aralkyl, which is substituted by G;
or R$^7$ and R$^8$ form an organic bridging group completing, together with the nitrogen atom, they are linked to, a heterocyclic ring of 5 to 7 ring atoms in total;
or said ring system is further anellated by one or more benzene rings
R$^2$, R$^3$, R$^4$ and R$^5$ are independently of each other H; C$_1$-C$_{18}$alkyl; C$_1$-C$_{18}$alkyl, which is substituted by E and/or interrupted by D; C$_5$-C$_{12}$cycloalkyl; C$_5$-C$_{12}$cycloalkyl, which is substituted by E; C$_6$-C$_{12}$aryl; C$_6$-C$_{18}$aryl, which is substituted by G; C$_2$-C$_{18}$heteroaryl; C$_2$-C$_{18}$heteroaryl, which is substituted by G; C$_1$-C$_{18}$alkoxy; C$_1$-C$_{18}$alkoxy, which is substituted by E and/or interrupted by D; C$_7$-C$_{18}$aralkyl; C$_7$-C$_{18}$aralkyl, which is substituted by G; NHR$^{18}$, NR$^{19}$R$^{20}$, COOH;
or R$^2$ and R$^3$, R$^4$ and R$^5$, or R$^2$ and R$^4$ form an organic bridging group completing, together with the carbon atom, they are linked to, a carbocyclic or heterocyclic ring of 5 to 12 ring atoms in total;
or two of R$^5$, which are linked to adjacent carbon atoms, form an organic bridging group completing, together with the carbon atom, they are linked to, a carbocyclic or heterocyclic ring of 5 to 12 ring atoms in total;
D is —CO—; —COO—; —S—; —SO—; —SO$_2$—; —O—; —NR$^{21}$—; —SiR$^{22}$R$^{23}$—; —POR$^{24}$—; —CR$^{25}$=CR$^{26}$—; or —C≡C—;
E is OR$^{27}$; SR$^{28}$; SOR$^{29}$; SO$_2$R$^{30}$; NR$^{31}$R$^{32}$; COR$^{33}$; COOR$^{34}$; CONR$^{35}$R$^{36}$; PO(R$^{37}$)$_2$; CN; or halogen; and
G is E or C$_1$-C$_{18}$alkyl;
R$^{18}$, R$^{19}$, R$^{20}$, R$^{21}$, R$^{22}$, R$^{23}$, R$^{24}$, R$^{25}$, R$^{26}$, R$^{27}$, R$^{28}$, R$^{29}$, R$^{30}$, R$^{31}$, R$^{32}$, R$^{33}$, R$^{34}$, R$^{35}$, R$^{36}$ and R$^{37}$ are independently of each other C$_1$-C$_{18}$alkyl; C$_1$-C$_{18}$alkyl, which is interrupted by —O—; C$_6$-C$_{18}$aryl; C$_6$-C$_{18}$aryl, which is substituted by C$_1$-C$_{18}$alkyl or C$_1$-C$_{18}$alkoxy; C$_7$-C$_{18}$aralkyl; C$_7$-C$_{18}$aralkyl, which is substituted by G; C$_2$-C$_{18}$heteroaryl;
or R$^{19}$ and R$^{20}$, R$^{31}$ and R$^{32}$, or R$^{35}$ and R$^{36}$ form an organic bridging group completing, together with the nitrogen atom, they are linked to, a heterocyclic ring of 5 to 7 ring atoms in total;
L is a n-valent leaving group,
n is an integer of 1, 2, 3 or 4; and
p is an integer of 1, 2, 3 or 4, wherein,
if n is 1, L is halogen, OH, OR$^{40}$, SR$^{40}$, OCOR$^{40}$, OCOOR$^{41}$, OCONR$^{42}$R$^{43}$, OCSNR$^{42}$R$^{43}$, OSO$_2$R$^{40}$, OSO$_3$R$^{40}$, NR$^{42}$R$^{43}$, S$^+$R$^{42}$R$^{43}$X$^-$, N$^+$R$^{42}$R$^{43}$R$^{44}$X$^-$, P$^+$R$^{42}$R$^{43}$X$^-$, NHCOR$^{40}$, OPO(OR$^{40}$)$_2$, OPO(R$^{46}$)(OR$^{47}$), OSi(R$^{40}$)$_3$;
wherein
R$^{40}$, R$^{42}$, R$^{43}$, R$^{44}$, R$^{45}$, R$^{46}$ and R$^{47}$ are independently of each other H, C$_1$-C$_{18}$alkyl or C$_1$-C$_{18}$alkyl, which is substituted by E and/or interrupted by D; C$_5$-C$_{12}$cycloalkyl, C$_5$-C$_{12}$cycloalkyl, which is substituted by E and/or interrupted by D; C$_6$-C$_{18}$aryl; C$_6$-C$_{18}$aryl, which is substituted by G; C$_7$-C$_{18}$aralkyl; C$_7$-C$_{18}$aralkyl, which is substituted by G; C$_2$-C$_{18}$heteroaryl; C$_2$-C$_{18}$heteroaryl, which is substituted by G;
or R$^{42}$ and R$^{43}$ form an organic bridging group completing, together with the nitrogen atom, they are linked to, a heterocyclic ring of 5 to 7 ring atoms in total;
or two of R$^{45}$ form a bridging group completing, together with the —OC—N—CO-group, they are linked to, a heterocyclic ring of 5 to 7 ring atoms in total;
R$^{41}$ is C$_1$-C$_{18}$alkyl or C$_1$-C$_{18}$alkyl, which is substituted by E and/or interrupted by D; C$_5$-C$_{12}$cycloalkyl, $C_5$-$C_{12}$cycloalkyl, which is substituted by E and/or interrupted by D; $C_6$-$C_{18}$aryl; $C_1$-$C_{18}$aryl, which is substituted by G; $C_2$-$C_{18}$heteroaryl; $C_2$-$C_{18}$heteroaryl, which is substituted by G;

$X^-$ is halide, hydroxide, $C_1$-$C_{18}$alkylsulfonate, $C_6$-$C_{18}$arylsulfonate, $R^{48}COO^-$, $HSO_4^-$ or ½ $SO_4^{2-}$, wherein $R^{48}$ is H, $C_1$-$C_{18}$alkyl or $C_1$-$C_{18}$alkyl, which is substituted by E and/or interrupted by D; $C_5$-$C_{12}$cycloalkyl, $C_5$-$C_{12}$cycloalkyl, which is substituted by E and/or interrupted by D; $C_6$-$C_{18}$aryl; $C_6$-$C_{18}$aryl, which is substituted by G; $C_2$-$C_{18}$heteroaryl; $C_2$-$C_{18}$heteroaryl, which is substituted by G;

if n is 2, L is —OCO—O—,

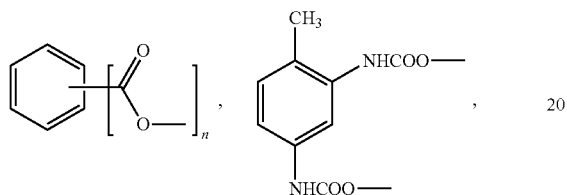

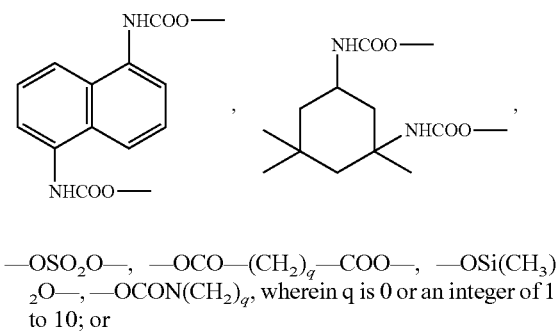

—OSO$_2$O—, —OCO—(CH$_2$)$_q$—COO—, —OSi(CH$_3$)$_2$O—, —OCON(CH$_2$)$_q$, wherein q is 0 or an integer of 1 to 10; or if n is 3 or 4, L is

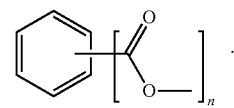

* * * * *